(12) United States Patent
Imamura

(10) Patent No.: US 9,044,167 B2
(45) Date of Patent: Jun. 2, 2015

(54) IMAGE PROCESSING DEVICE, IMAGING SYSTEM, IMAGE PROCESSING METHOD, AND PROGRAM FOR CAUSING COMPUTER TO PERFORM IMAGE PROCESSING

(75) Inventor: Hiroshi Imamura, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 201 days.

(21) Appl. No.: 13/402,617

(22) Filed: Feb. 22, 2012

(65) Prior Publication Data

US 2012/0218516 A1 Aug. 30, 2012

(30) Foreign Application Priority Data

Feb. 25, 2011 (JP) ................................. 2011-040272

(51) Int. Cl.
*A61B 3/14* (2006.01)
*A61B 3/10* (2006.01)
*A61B 3/12* (2006.01)

(52) U.S. Cl.
CPC ............. *A61B 3/1025* (2013.01); *A61B 3/1241* (2013.01)

(58) Field of Classification Search
CPC ........ A61B 3/14; A61B 3/145; A61B 3/1233; A61B 3/1241; A61B 5/026; A61B 5/02007; A61B 5/489; G06T 2207/10056; G06T 2207/30041; G06T 2207/30101
USPC ........................... 351/205, 206, 211–216, 221
See application file for complete search history.

(56) References Cited

U.S. PATENT DOCUMENTS

| 6,890,076 | B2 | 5/2005 | Roorda |
| 2005/0254008 | A1 | 11/2005 | Ferguson |
| 2007/0291230 | A1 | 12/2007 | Yamaguchi |
| 2009/0303438 | A1* | 12/2009 | Yamada et al. ............... 351/206 |
| 2011/0234975 | A1 | 9/2011 | Hirose |
| 2012/0033227 | A1* | 2/2012 | Bower et al. .................. 356/479 |

FOREIGN PATENT DOCUMENTS

WO  WO2009/015295 A1  1/2009

OTHER PUBLICATIONS

Johnny Tam, Austin Roorda, "Enhanced Detection of Cell Paths in Spatiotemporal Plots for Noninvasive Microscopy of the Human Retina", Proceedings of 2010 IEEE International Symposium on Biomedical Imaging, pp. 584-587, Apr. 2010.
Johnny Tam, Austin Roorda, "Pulsatility of parafoveal capillary leukocytes", Experimental Eye Research 88 (2009) pp. 356-360.
Joy A. Martin, Austin Roorda, "Direct and Noninvasive Assessment of Parafoveal Capillary Leukocyte Velocity", 2005 by the American Academy of Ophthalmology, ISSN 0161-6420/05, vol. 112, No. 12, pp. 2219-2223.

(Continued)

*Primary Examiner* — Mahidere Sahle
(74) *Attorney, Agent, or Firm* — Canon U.S.A. Inc. IP Division

(57) ABSTRACT

An image processing device includes a first identification unit configured to identify the spatial configuration of a vessel in an object to be imaged, a second identification unit configured to identify information on a blood flow rate of the vessel based on an SLO moving image obtained by signal light that has a focus position deeper than at least a part of the area of the vessel, and an acquisition unit configured to acquire information on a blood flow of the vessel based on the identified area and the information on the blood flow rate.

17 Claims, 13 Drawing Sheets

(56) References Cited

OTHER PUBLICATIONS

Johnny Tam et al., "Noninvasive Visualization and Analysis of Parafoveal Capillaries in Humans", Investigative Ophthalmology & Visual Science, Mar. 2010, vol. 51, No. 3, pp. 1691-1698.

Martin, Joy A et al., "Direct and Noninvasive Assessment of Parafoveal Capillary Leukocyte Velocity", American Academy of Opthalmology, vol. 112, No. 12, Dec. 2005, pp. 2219-2224, XP027635514.

* cited by examiner

FIG. 7A
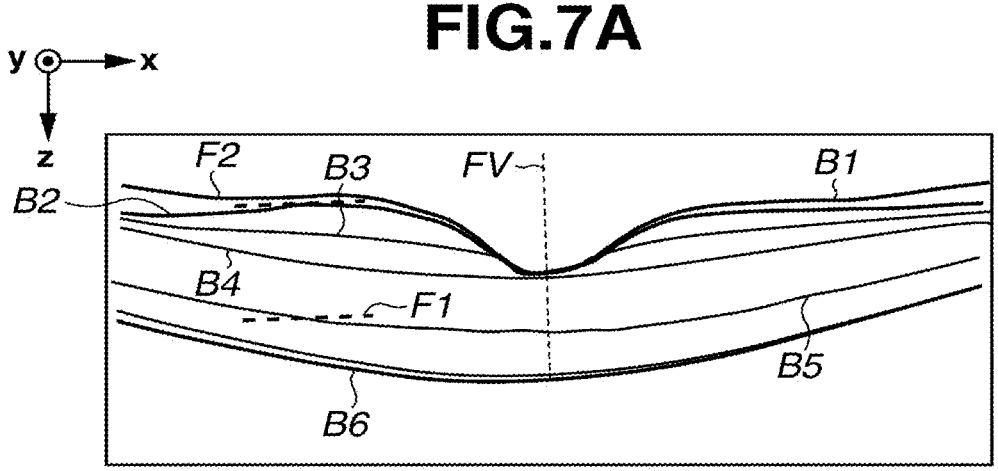
FIG. 7B
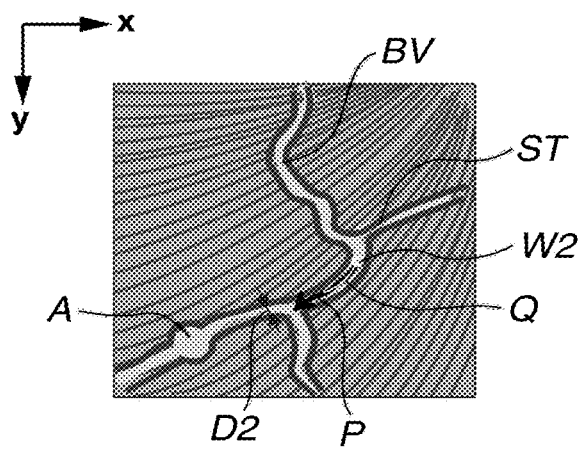
FIG. 7C
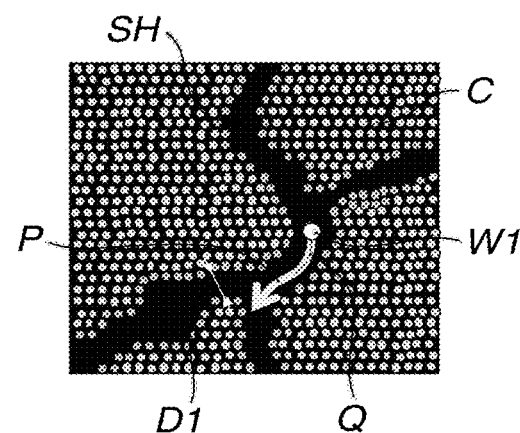
FIG. 7D
| FOCUS POSITION [μm] | LAYER | IMAGE FEATURE |
|---|---|---|
| F2 | NERVE FIBER LAYER | NERVE FASCICLES, RETINAL VESSELS |
| F1 | VISUAL CELL LAYER | VISUAL CELLS, BLOOD CELL FEATURES |

FIG.10A
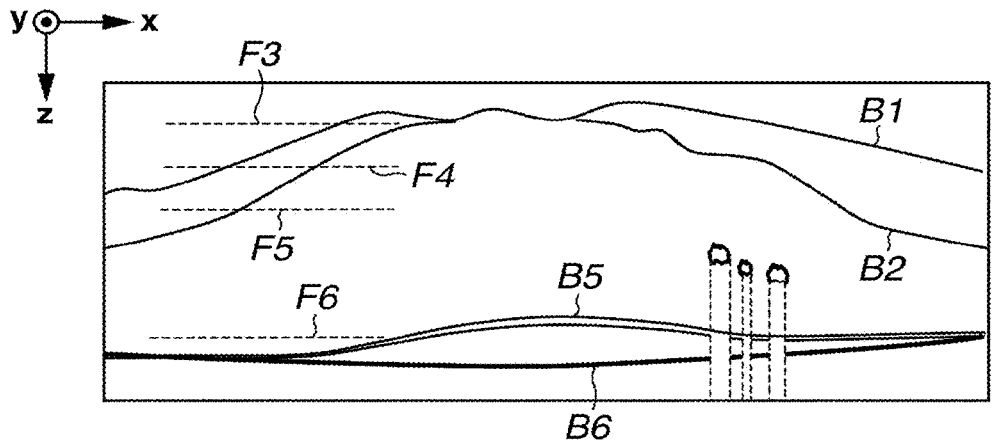
FIG.10B
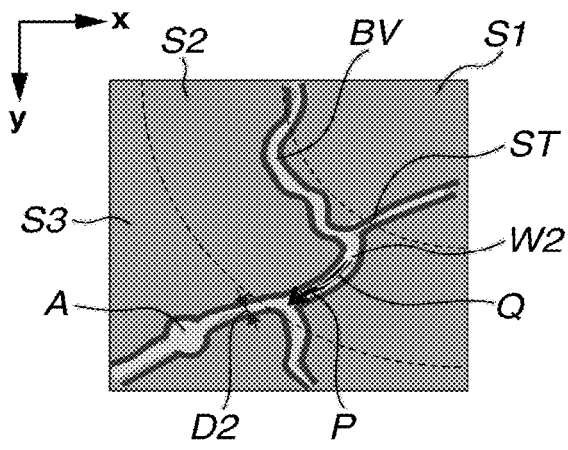
FIG.10C
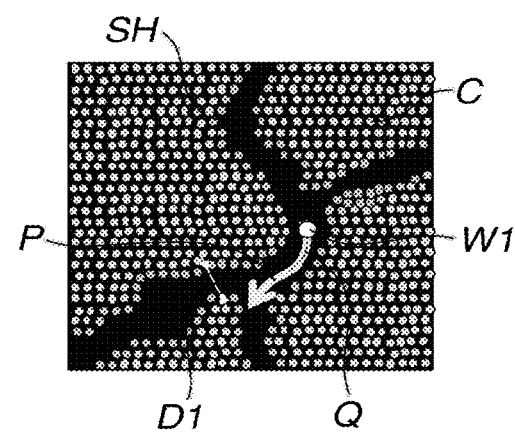
FIG.10D
| LAYER | IMAGE FEATURE |
|---|---|
| NERVE FIBER LAYER | NERVE FASCICLES, RETINAL VESSELS |
| VISUAL CELL LAYER | VISUAL CELLS, BLOOD CELL FEATURES |

IMAGE PROCESSING DEVICE, IMAGING SYSTEM, IMAGE PROCESSING METHOD, AND PROGRAM FOR CAUSING COMPUTER TO PERFORM IMAGE PROCESSING

BACKGROUND OF THE INVENTION

1. Field of the Invention

The present disclosure relates to image processing for processing eye images.

2. Description of the Related Art

An eye examination is widely practiced for early diagnosis of lifestyle related diseases and diseases that rank high among the leading causes of blindness. A scanning laser ophthalmoscope (SLO), hereinafter referred to as an SLO imaging device, is an ophthalmologic instrument that uses the principles of a confocal laser microscope. An SLO imaging device performs raster scanning of the fundus with measurement laser light and acquires a planar image of the retina from the intensity of return light with high resolution and high speed.

There have been developed some SLO imaging devices that have an adaptive optics (AO) system for measuring aberrations of the eye to be examined with a wavefront sensor and correcting aberrations of measurement light occurring in the eye to be examined and aberrations of return light with a wavefront correction device. Such SLO imaging devices are referred to as AO-SLO imaging devices. AO-SLO imaging devices enable image acquisition with high lateral resolution, allowing detection of retinal capillary vessels and visual cells. Johnny Tam and Austin Roorda, "Enhanced Detection of Cell Paths in Spatiotemporal Plots for Noninvasive Microscopy of the Human Retina," Proceedings of 2010 IEEE International Symposium on Biomedical Imaging, pp. 584-587, April 2010, discusses a technique of recognizing a moving range of blood cells as a vessel area from an SLO image that is focused near visual cells of the healthy eye, and measuring blood flow behavior including the moving speed of blood cells. However, SLO images focused near visual cells do not always allow accurate identification of vessels because vessels themselves are not in focus.

SUMMARY OF THE INVENTION

According to an aspect of the present invention, an image processing device includes a first identification unit configured to identify the spatial configuration of a vessel in an object to be imaged, a second identification unit configured to identify information on a blood flow rate of the vessel based on an SLO moving image obtained by signal light that has a focus position deeper than at least a part of the area of the vessel, and an acquisition unit configured to acquire information on a blood flow of the vessel based on the identified area and the information on the blood flow rate.

The embodiment extends to methods, apparatus and/or use substantially as herein described with reference to the accompanying drawings. Any feature in one aspect of the invention may be applied to other aspects of the invention, in any appropriate combination. In particular, features of method aspects may be applied to apparatus aspects, and vice versa.

Further preferred features and aspects of the present embodiment will become apparent from the following detailed description of exemplary embodiments with reference to the attached drawings.

BRIEF DESCRIPTION OF THE DRAWINGS

FIGS. 7A, 7B, 7C, and 7D are diagrams for describing the content of image processing according to an exemplary embodiment.

FIGS. 10A, 10B, 10C, and 10D are diagrams for describing the content of image processing according to a third exemplary embodiment.

DESCRIPTION OF THE EMBODIMENTS

Various exemplary embodiments, and features will be described in detail below with reference to the drawings.

Figure 1:
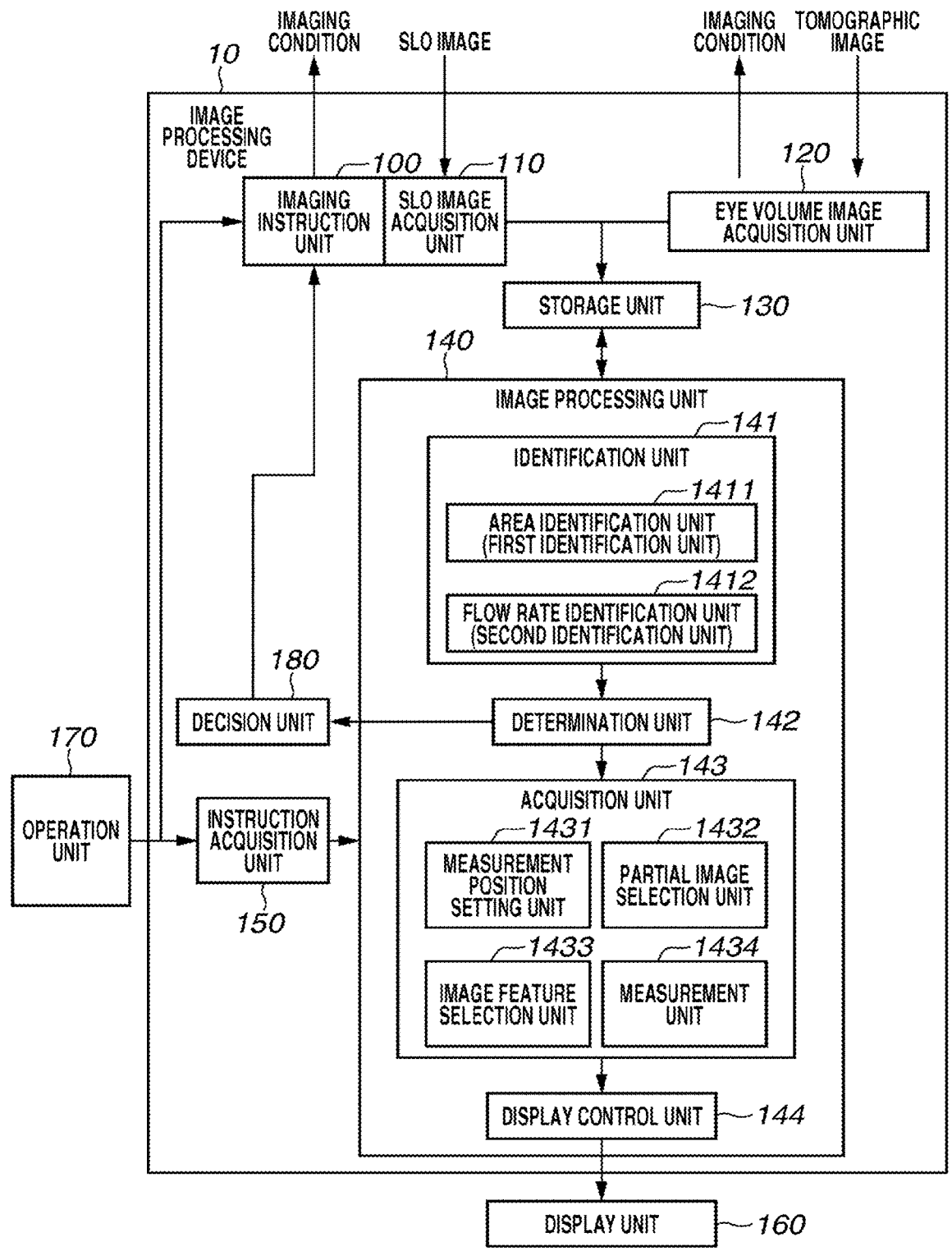
FIG. 1 is a block diagram illustrating an example of the functional configuration of an image processing device according to an exemplary embodiment.

Referring to FIG. 1, the functional configuration of an image processing device 10 according to the present first exemplary embodiment will be described. FIG. 1 is a block diagram illustrating the functional configuration of the image processing device 10. The image processing device 10 include an imaging instruction unit 100, an SLO image acquisition unit 110, an eye volume image acquisition unit 120, a storage unit 130, an image processing unit 140, and an instruction acquisition unit 150. A display unit 160 and an operation unit 170 are connected to the image processing device 10.

The image processing unit 140 includes an identification unit 141, a decision unit 142, an acquisition unit 143, a display control unit 144, and a determination unit 180. The image processing unit 140 processes images of an eye, which is an object to be imaged. The identification unit 141 includes an area specification unit (first identification unit) 1411 and a flow rate specification unit (second identification unit) 1412. The SLO image acquisition unit 110 acquires a plurality of SLO images by using beams of signal light of different focus depths. The first identification unit 1411 and the second identification unit 1412 each identify image features of the eye from such a plurality of SLO images. The acquisition unit 143 includes a measurement position setting unit 1431, a partial image selection unit 1432, an image feature selection unit 1433, and a measurement unit 1434. The acquisition unit 143 acquires diagnostically useful indexes or images based on identified image features.

Figure 2:
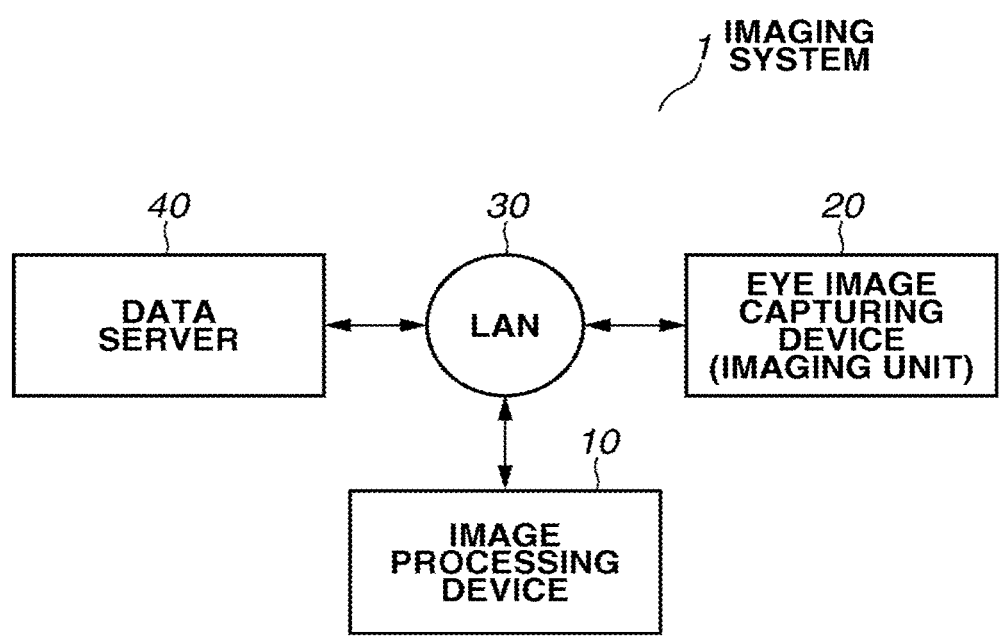
FIG. 2 is a block diagram illustrating an example of the configuration of a system that includes an image processing device 10 according to an exemplary embodiment.

FIG. 2 is a block diagram of an imaging system that includes the image processing device 10 according to the present exemplary embodiment. As illustrated in FIG. 2, the image processing device 10 is connected with an eye image capturing device 20 and a data server 40 through a local area network (LAN) 30 which is constituted by optical fibers, a universal serial bus (USB), and/or an Institute of Electrical and Electronic Engineers (IEEE) 1394 interface. The image processing device 10 may be connected with such devices through an external network such as the Internet.

The eye image capturing device (imaging unit) 20 includes an SLO imaging unit (SLO imaging device) for capturing fundus images (SLO images) and an optical coherence tomography (OCT) image capturing unit (OCT imaging device) for capturing volume images (OCT images). The eye image capturing device 20 captures a still image or a moving image as an SLO image, and transmits the captured SLO image to the image processing device 10 and the data server 40. The OCT image capturing unit is configured as a time domain system or Fourier domain system. The OCT image capturing unit captures three-dimensional tomographic images of an eye to be examined according to a not-illustrated operator's operation. The OCT image capturing unit transmits the resulting volume images to the image processing device 10 and the data server 40. The OCT image capturing unit is an optional component of the eye image capturing device 20. The eye image capturing device 20 may include only the SLO image capturing unit.

The data server 40 is a server for retaining SLO images and volume images of an eye to be examined, an eye's image features (to be described later—hereinafter referred to as eye features), and data on pulse waves and fixation target positions at the time of SLO image capturing. The data server 40 stores SLO images and volume images of an eye to be examined that are output by the eye image capturing device 20, and eye features that are output by the image processing device 10. The data server 40 transmits data (SLO images, volume images, and eye features) of an eye to be examined, normal value data on eye features, and the values of pulse waves of the eye to be examined and fixation target positions to the image processing device 10 in response to a request from the image processing device 10.

Figure 3:
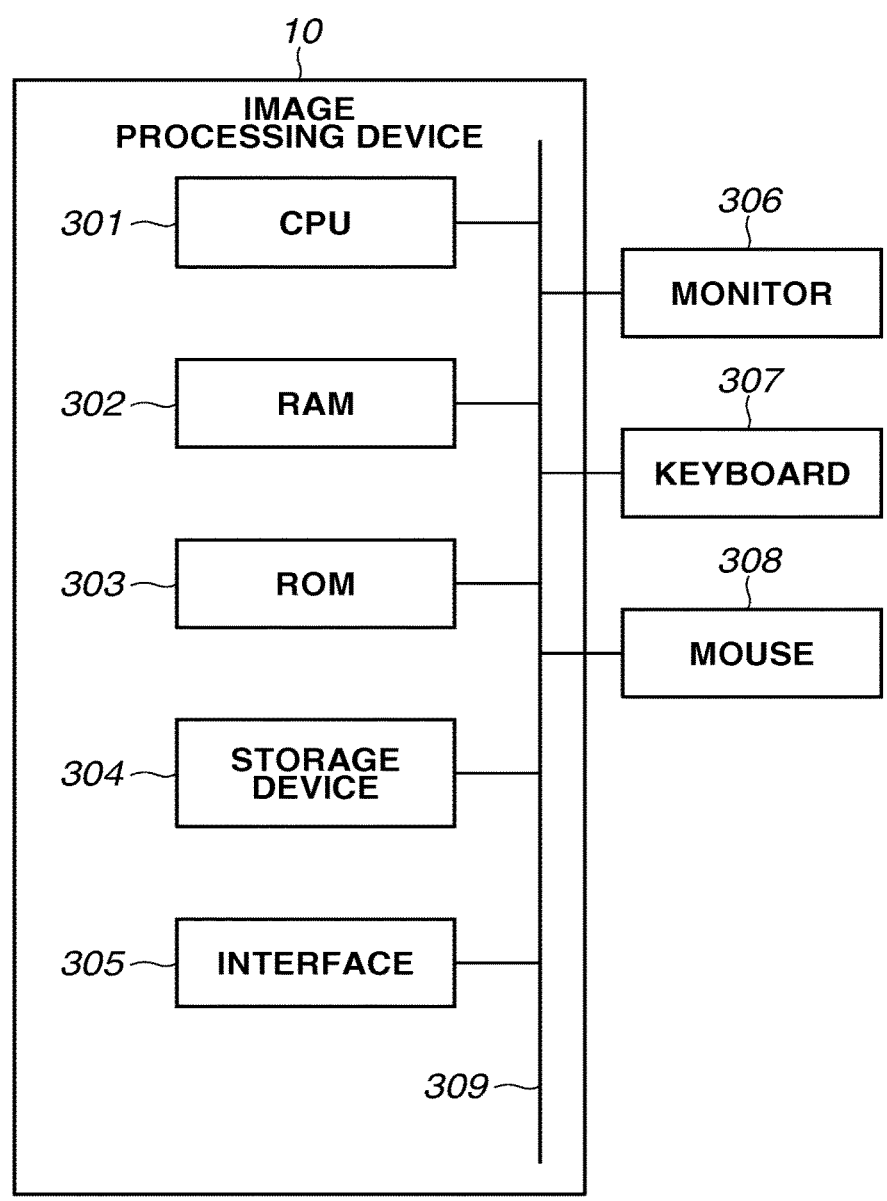
FIG. 3 is a block diagram illustrating an example of the hardware configuration of an image processing device.

Next, the hardware configuration of the image processing device 10 having the foregoing functional configuration will be described with reference to FIG. 3. In the example of FIG. 3, the image processing device 10 includes a central processing unit (CPU) 301, a memory (random access memory or RAM) 302, a control memory (read-only memory, or ROM) 303, a storage device 304, and an interface 305, which are connected by a bus 309. A monitor 306, a keyboard 307, and a mouse 308 are connected to the image processing device 10.

The storage device 304 contains a control program for implementing processing of the image processing device 10 illustrated in FIG. 6 or FIG. 9 to be described later, and data for use in executing the control program. The control program and data are loaded into the RAM 302 through the bus 309 under control of the CPU 301 when needed. The CPU 301 executes the control program to implement the foregoing functions in cooperation with the above-mentioned hardware. For example, the storage device 304 functions as the storage unit 130 of FIG. 1. The keyboard 307 or the mouse 308 functions as the operation unit 170. The monitor 306 functions as the display unit 160. The processing of the image processing device 10 is achieved by such cooperation of software and hardware.

Figure 4:
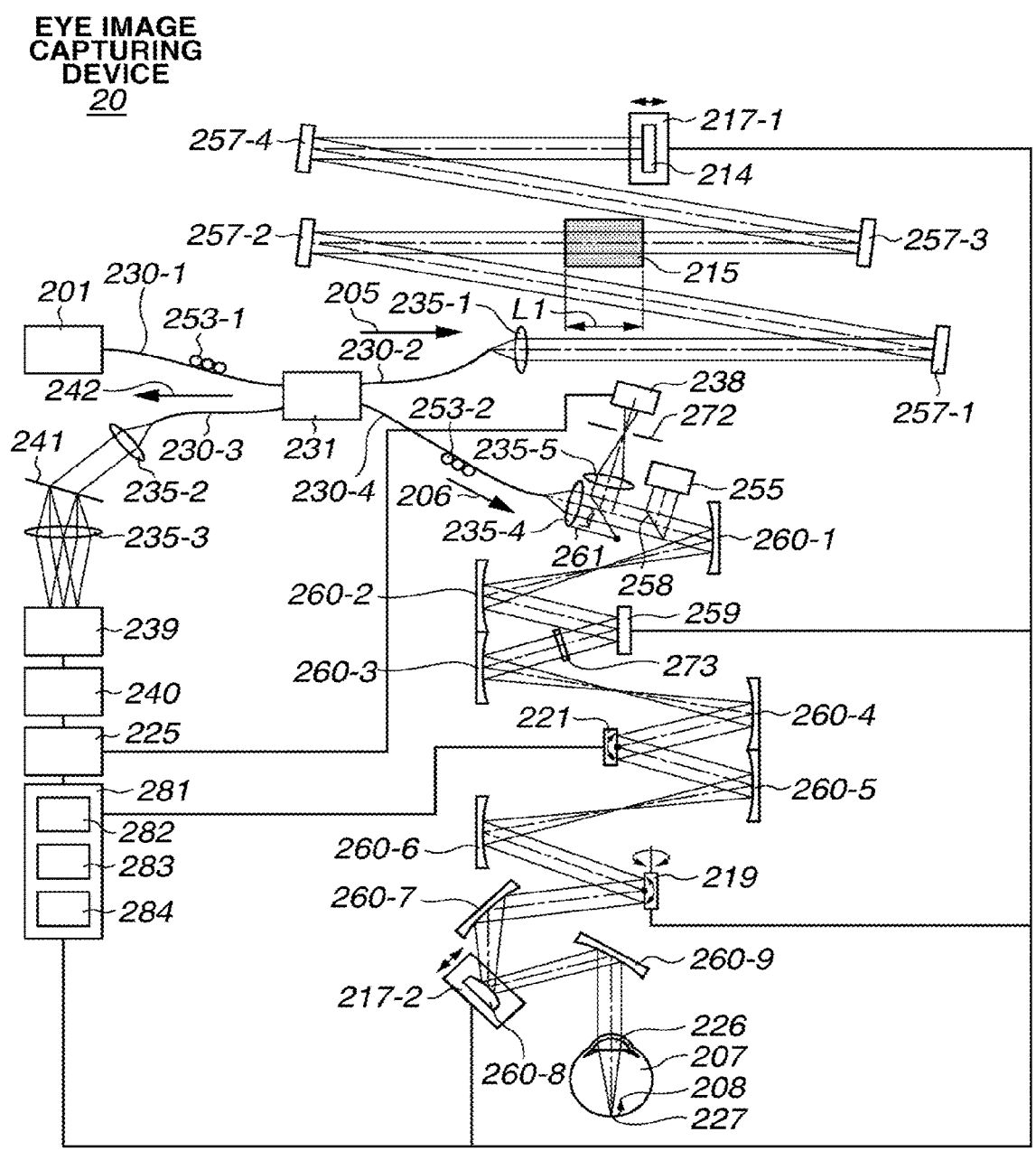
FIG. 4 is a diagram for describing an overall configuration of an eye image capturing device.

If the eye image capturing device 20 is configured to include only the SLO image capturing unit without the OCT image capturing unit, the image processing device 10 need not include the eye volume image acquisition unit 120. The present example deals with a case where no layer shape abnormality is observed. The partial image selection unit 1432 thus performs no particular processing. FIG. 4 illustrates the configuration of the eye image capturing device 20.

A light source 201 emits light. An optical coupler 231 divides the light into reference light 205 and measurement light 206. The measurement light 206 is guided to an eye to be examined 207, which is an object to be observed, through a single mode fiber 230-4, a spatial light modulator 259, an XY scanner 219, an X scanner 221, and spherical mirrors 260-1 to 260-9. Reflected and scattered by the eye to be examined 207, the measurement light 206 becomes return light 208. The return light 208 is incident on a detector 238 or a line sensor 239. The detector 238 coverts the light intensity of the return light 208 into a voltage, whose signal is used to construct a planar image of the eye to be examined 207.

The reference light 205 and the return light 208 are multiplexed and incident on the line sensor 239, in which a tomographic image of the eye to be examined 207 is constructed. Variable geometry mirrors may be used as long as wavefront aberrations can be corrected.

The light source 201 is a super luminescent diode (SLD), a typical low-coherent light source. The light source 201 has a wavelength of 830 nm and a bandwidth of 50 nm. A low-coherent light source is selected in order to acquire a plane image with less speckle noise. While an SLD is selected here, any type of light source that can emit low-coherent light may be used, including an amplified spontaneous emission (ASE) light source.

In terms of eye measurement, near infrared rays have suitable wavelengths. The wavelength has an effect on the lateral resolution of the resulting planar image. Accordingly, the shorter, the more desirable. In the present exemplary embodiment, the wavelength of 830 nm is employed. Other wavelengths may be selected depending on the measurement part to be observed. The SLD, a low-coherent light source, is also suited to capturing tomographic images.

Next, the optical path of the reference light 205 will be described. The reference light 205 divided by the optical coupler 231 is guided to a lens 235-1 through a single mode fiber 230-2. The lens 235-1 adjusts the reference light 205 into a parallel beam having a beam diameter of 4 mm. The reference light 205 is then guided by mirrors 257-1 to 257-4 to a mirror 214, a reference mirror. The optical path length of the reference light 205 is adjusted to be generally the same as that of the measurement light 206. Such adjustment causes interference between the reference light 205 and the measurement light 206.

The reference light 205 is reflected by the mirror 215 and guided to the optical coupler 231 again. Here, the reference light 205 is passed through a dispersion compensation glass 215. The dispersion compensation glass 215 is intended to compensate for the dispersions that occur when the measurement light 206 is reciprocated through the eye to be examined 207, for the reference light 205. Let L1=23 mm, which is assumed to be a typical value of the average eyeball diameter of the Japanese. A motor-driven stage 217-1 can be moved in directions illustrated by the arrows. Such movements enable adjustment and control of the optical path length of the reference light 205. A personal computer 225 controls the motor-driven stage 217-1 through a motor-driven stage driver 283 which is included in a driver unit 281.

Next, the optical path of the measurement light 206 will be described. The measurement light 206 divided by the optical coupler 231 is guided to a lens 235-4 through the single mode fiber 230-4. The lens 235-4 adjusts the measurement light 206 into a parallel beam having a beam diameter of 4 mm. Polarization controllers 253-1 and 253-2 can adjust the polarization state of the measurement light 206. The polarization state of the measurement light 206 is adjusted to linear polarization in a direction parallel to the plane of the diagram.

The measurement light 206 passes through a movable beam splitter 261 and a beam splitter 258. The measurement light 206 is then incident, via the spherical mirrors 260-1 and 260-2, upon the spatial light modulator 259 for modulation. The spatial light modulator 259 is a modulator that performs modulation by utilizing the orientation of liquid crystals. To modulate the phase of linear polarization (P-polarization), the spatial light modulator 259 is situated in a direction parallel to the plane of the diagram, so as to coincide with the direction of polarization of the measurement light 206.

The measurement light 206 passes through a polarization plate 273, and is incident on a mirror of the X scanner 221 via the spherical mirrors 260-3 and 260-4. The role of the polarization plate 273 is to guide to the spatial light modulator 259 only a component of the return light 208 linearly polarized in a direction parallel to the plane of the diagram. The X scanner 221 is a scanner for scanning using the measurement light 206 in a direction parallel to the plane of the diagram. A resonant scanner is used here. The X scanner 221 has a driving frequency of approximately 7.9 kHz.

The measurement light 206 is incident on a mirror of the XY scanner 219 via the spherical mirrors 260-5 and 260-6. While the XY scanner 219 is illustrated as a single mirror, the XY scanner 219 actually includes two mirrors, i.e., an X scanning mirror and a Y scanning mirror, which are arranged adjacent to each other. The center of the measurement light 206 is adjusted to coincide with the rotation center of the mirror of the XY scanner 219. The XY scanner 219 has a variable driving frequency of up to 500 Hz.

The spherical mirrors 260-7 to 260-9 constitute an optical system for scanning the retina 227. The role of the optical system is to scan the retina 227 using the measurement light 206 with a fulcrum near the cornea 226.

While the measurement light 206 has a beam diameter of 4 mm, the beam diameter may be increased in order to acquire tomographic images with higher resolution.

A motor-driven stage 217-2 can be moved in directions illustrated by the arrows. Such movements enable adjustment and control of the position of the accompanying spherical mirror 260-8. Like the motor-driven stage 217-1, the motor-driven state 217-2 is controlled by the motor-driven stage driver 283.

The position of the spherical mirror 260-8 can be adjusted to focus the measurement light 206 on a predetermined layer of the retina 227 for observation. In an initial state, the position of the spherical mirror 260-8 is adjusted so that the measurement light 206 is incident on the cornea 226 as a parallel beam.

The eye image capturing device 20 can handle situations where the eye to be examined 207 has a refractive error. The measurement light 206 incident on the eye to be examined 207 is reflected and scattered by the retina 227 and becomes return light 208. The measurement light 206 (return light 208) is then guided to the optical coupler 231 again, and reaches the line sensor 239.

A part of the return light 208 is reflected by the movable beam splitter 261, and guided to the detector 238 through a lens 235-5. A light blocking plate 272 has a pinhole. The role of the light blocking plate 272 is to block unnecessary portions of the return light 208 that are not focused on the retina 227. The light blocking plate 272 is located conjugate to the in-focus position of the lens 235-5. The pinhole in the light blocking plate 272 has a diameter of 50 μm, for example. An example of the detector 238 is an avalanche photo diode (APD) which is a high-speed high-sensitivity optical sensor.

A part of the return light 108 divided by the beam splitter 258 is incident on a wavefront sensor 255. The wavefront sensor 255 is a Shack-Hartmann wavefront sensor.

The spherical mirrors 260-1 to 260-9 are arranged so that the XY scanner 219, the X scanner 221, the cornea 226, the wavefront sensor 255, and the spatial light modulator 259 are optically conjugate. Such arrangement allows the wavefront sensor 255 to measure aberrations of the eye to be examined 207. The arrangement also allows the spatial light modulator 259 to correct aberrations of the eye to be examined 207. Based on the aberrations sensed, the spatial light modulator 259 is controlled in real time to correct aberrations occurring in the eye to be examined 207. This enables acquisition of tomographic images with even higher lateral resolution.

Next, the configuration of measurement systems will be described. The eye image capturing device 20 can acquire tomographic images (OCT images) and planar images (SLO images). First, a measurement system for tomographic images will be described.

The return light 208 is multiplexed by the photo coupler 231. The multiplexed light 242 is guided to a transmissive grating 241 through a single mode fiber 230-3 and a lens 235-2. The transmissive grating 241 splits the multiplexed light 242 by wavelength. The resulting beams are incident on the line sensor 239 through a lens 235-3.

The line sensor 239 converts the intensities of light at respective positions (wavelengths) into voltages. A frame grabber 240 converts the voltage signals into digital values. The personal computer 225 constructs a tomographic image of the eye to be examined 207 from the digital values. The line sensor 239 has 1024 pixels, and can acquire the intensities of the multiplexed light 242 at respective wavelengths (division into 1024 parts).

Next, a measurement system for planar images will be described.

A part of the return light 208 is reflected by the movable beam splitter 261. The light blocking plate 272 blocks unnecessary portions of the reflected light. The resulting light reaches the detector 238, which converts the intensity of the light into an electrical signal. The personal computer 225 performs data processing on the resulting electrical signal in synchronization with scanning signals of the X scanner 221 and the XY scanner 219, thereby forming a planar image. A part of the return light 208 divided by the beam splitter 258 is incident on the wavefront sensor 255. The wavefront sensor 255 measures aberrations of the return light 208 and produces an image signal. The personal computer 225 obtains the image signal and calculates aberrations. The calculated aberrations are expressed by using a Zernike polynomial, which represents the aberrations of the eye to be examined 207.

The Zernike polynomial includes a tilt term, a defocus term, an astigmatic (astigmatic aberration) term, a coma term, and a trefoil term.

Next, a method of acquiring a tomographic image (OCT image) by using the eye image capturing device 20 will be described with reference to FIGS. 5A to 5C.

The eye image capturing device 20 can acquire a tomographic image of the retina 227 by controlling the XY scanner 219, using the X scanner 221 as a fixed mirror, and acquiring an interference pattern with the line sensor 239. The eye image capturing device 20 controls the movable beam splitter 261 so that the return light 208 is not guided to the detector 238. The personal computer 225 controls the X scanner 221 and the XY scanner 219 through an optical scanner driver 282 which is included in the driver unit 281. A method of acquiring a tomographic image (along a plane parallel to the optical axis) of the retina 227 will be described below.

Figure 5A:
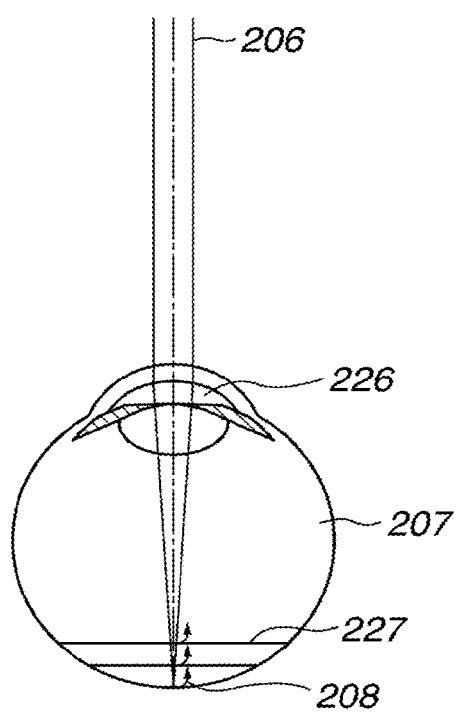
FIGS. 5A, 5B, and 5C are diagrams for describing a method by which the eye image capturing device acquires an image.

FIG. 5A is a schematic diagram of an eye to be examined 207, illustrating a state where the eye to be examined 207 is observed by the eye image capturing device 20. As illustrated in FIG. 5A, the measurement light 206 passes through the cornea 226 and is incident on the retina 227. The measurement light 206 is reflected and scattered at various positions and becomes return light 208. The return light 208 reaches the line sensor 239 with time delays in respective positions.

The light source 201 has a wide bandwidth and a short coherent length. The line sensor 239 can thus detect an interference pattern when the reference light path and the measurement light path have generally the same optical path lengths. As described above, the line sensor 239 acquires an interference pattern in a spectral domain on a wavelength axis.

The eye image capturing device 20 then converts the interference pattern, which is information on the wavelength axis, into an interference pattern on an optical frequency axis in consideration of the characteristics of the line sensor 239 and the transmissive grating 241. The eye image capturing device 20 further performs an inverse Fourier transform on the converted interference pattern on the optical frequency axis, thereby acquiring information in a depth direction. The eye image capturing device 20 can drive the XY scanner 219 as illustrated in FIG. 5B while detecting an interference pattern. This enables acquisition of interference patterns at respective positions in the X-axis direction, i.e., acquisition of information in the depth direction on each position in the X-axis direction. As a result, the eye image capturing device 20 acquires a two-dimensional distribution of the intensity of the return light 208 on the XZ plane, which is a tomographic image 232 (FIG. 5C).

As has been described above, a tomographic image 232 itself contains an array of intensities of the return light 208. The intensities are applied to and displayed in a gray scale, for example. A tomographic image 232 has a length of 700 μm in the X direction. FIG. 5C illustrates the resulting tomographic image 232 with emphasis only on boundaries. The tomographic image 232 shows a retinal pigment epithelium 246, a nerve fiber layer 247, and a vessel 278.

Next, a method of acquiring a planar image (SLO image) by using the eye image capturing device 20 will be described.

The eye image capturing device 20 can acquire a planar image of the retina 227 by operating and controlling the XY scanner 219 in the Y-axis direction and fixing the XY scanner 219 in the X direction, operating and controlling the X scanner 221, and acquiring the intensity of the return light 208 with the detector 238. The personal computer 225 controls the X scanner 221 and the XY scanner 219 through the optical scanner driver 282 in the driver unit 281. While acquiring a planar image, the eye image capturing device 20 can control the spatial light modulator 259 according to aberrations of the eye to be examined 207, measured by the wavefront sensor 255, thereby correcting aberrations occurring in the eye to be examined 207. The eye image capturing device 20 can also control the spatial light modulator 259 in real time while acquiring a planar image.

Figure 5B:
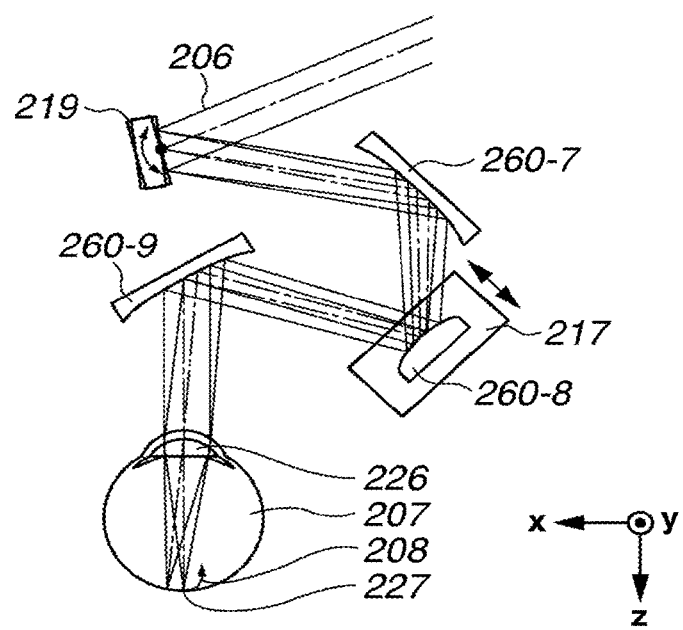
Figure 5C:
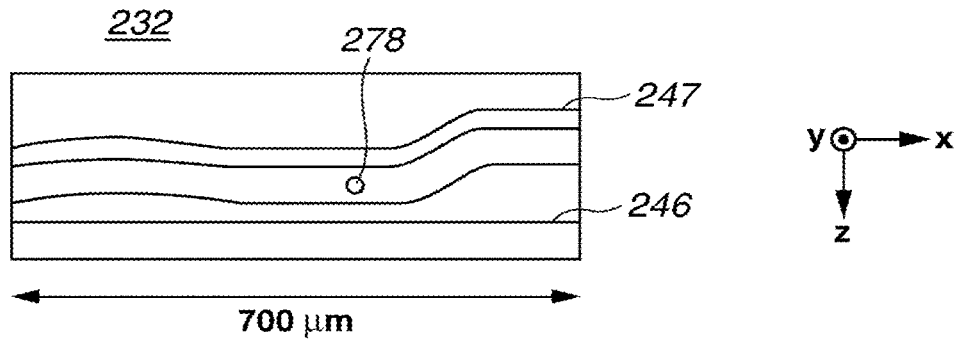

In the present exemplary embodiment, the eye image capturing device 20, when acquiring an SLO image, moves the spherical mirror 260-8 in the arrowed directions as illustrated in FIG. 5B to adjust a focus position. Specifically, the eye image capturing device 20 moves the spherical mirror 260-8 to focus on a position where an outer boundary B6 (see FIG. 7 to be described later) of the retinal pigment epithelium 246 has highest luminance. This can set the focus position to B6. Then, the eye image capturing device 20 can move the spherical mirror 260-8 by predetermined amounts to set the focus position to different positions. For example, the eye image capturing device 20 may be designed so that the focus position moves by 5 μm when the spherical mirror 260-8 is moved by 1 mm. It should be noted that the method of focus adjustment is not limited thereto. For example, the spatial light modulator 259 may be used for focus adjustment. Alternatively, a variable geometry mirror may be employed for aberration correction to perform focus adjustment. Alternatively, the entire optical system may be configured as a dioptric system using lenses instead of spherical mirrors, and a focus lens may be moved for adjustment.

As described above, an AO-SLO imaging device can obtain images of capillary vessels in the vicinity of the macula, nerve fibers, and visual cells which are smaller than vessels to be imaged by conventional Fourier domain OCTs and fundus cameras.

The functions of the blocks constituting the image processing device 10 will be described in association with an execution procedure of the image processing device 10 illustrated in the flowchart of FIG. 6. The above-described image processing device 10 measures the behavior of blood cells (blood flow) from an SLO moving image which is captured at a predetermined focus position. The SLO moving image is an image that is captured with its focus set to a position deeper than at least a part of vessel positions, i.e., a vessel position to be measured for the sake of observation of blood cell behavior. The image processing device 10 identifies the behavior of blood cells from such an SLO moving image. When focusing near a visual cell layer is performed, visual cell groups can be observed with high luminance. However, in areas where retinal vessels are present, various blood cell components preclude the measurement light from reaching the SLO focus depth, and shadows of low luminance are formed on the resulting SLO image. Boundaries of the shadow blur in areas corresponding to retinal vessel walls. On the other hand, some blood cell components form no shadow. Such components produce high luminance even in areas where retinal vessels are present. Blood cell components that form no shadow are considered to be white blood cells. The movement of high luminance areas in a vessel can be observed with a high contrast. Measuring the moving speed of high luminance areas in a vessel is equivalent to measuring the moving speed of white blood cells.

As described above, an SLO moving image that is focused near visual cells allows precise observation of blood cell behavior. However, since vessels themselves are not in focus, it may be not possible to identify vessel areas with high precision.

Then, the image processing device 10 determines whether the focus position needs to be changed to re-capture an SLO image, based on the result of acquisition of eye's image features. If it is determined to be necessary to change the focus position for re-capturing, the image processing device 10 determines image capturing parameters related to the changing of the focus position based on the eye features. An SLO image is then re-captured focusing in particular on an area where vessels are present. The image processing device 10 identifies vessel areas from the resulting image. Consequently, the image processing device 10 can measure the behavior of blood cells with higher accuracy and reliability from the information on the behavior of blood cells and the information on the blood cell areas.

An overview of the processing according to the present exemplary embodiment will be given with reference to FIGS. 7A to 7D. FIG. 7A is a diagram for describing focus positions to be set in the present exemplary embodiment. FIG. 7B illustrates an example of an SLO image and retinal vessels that are obtained when the focus position is set near the nerve fiber layer. FIG. 7C illustrates an example of an SLO image and retinal vessel shadows that are obtained when the focus position is set near a boundary between inner and outer segments of visual cells. FIG. 7D illustrates table information which includes focus depth values, the types of retinal layers that are observed at the focus depths, and image features that are obtained through analysis of SLO images focused on the respective retinal layers.

In the present exemplary embodiment, the image processing device 10 extracts retinal vessel shadows SH from an SLO moving image M1 that is captured with the focus position set near visual cells C. The image processing device 10 then attempts to detect white blood cells (second tissue) in the retinal vessel shadows SH and measure the speed thereof. If the SLO moving image M1 (second SLO image) at the focus position is determined to be not suited to identify vessel areas (first tissue), the image processing device 10 changes the focus position to near the nerve fiber layer. An SLO still image M2 (first SLO image) is then captured at that focus position. If the SLO moving image M1 includes any location where the result of detection of a vessel area falls below a threshold in reliability, the image processing device 10 examines the same x and y positions of the SLO still image M2 for a luminance value. The image processing device 10 then determines boundaries of high luminance components detected on both the SLO images as retinal vessel areas. Thus, more robust measurement of the behavior of white blood cells can be made from the SLO moving image M1 whose focus position is set near visual cells C.

In step S610, the SLO image acquisition unit 110 requests the eye image capturing device 20 to acquire an SLO image (still image or moving image) that is set to a certain focus position. If needed, the eye volume image acquisition unit 120 may request the eye image capturing unit 20 to acquire an eye volume image. In the present exemplary embodiment, only an SLO moving image M1 (frame number i=1, 2, ..., N) is input. As illustrated in FIG. 7A, a focus position F1 near a boundary between inner and outer segments of visual cells is set.

In response to the acquisition request, the eye image capturing device 20 acquires and transmits a corresponding SLO moving image M1. The SLO image acquisition unit 110 receives the SLO moving image M1 from the eye image capturing device 20 through the LAN 30. The SLO image acquisition unit 110 stores the received SLO moving image M1 in the storage unit 130.

In step S620, the identification unit 141 acquires eye features from the image acquired in step S610. In the present exemplary embodiment, only the SLO moving image M1 is acquired in step S610. As information on a blood flow rate in the eye, the flow rate specification unit (second identification unit) 1412 acquires data on retinal vessel shadow areas SH and a high luminance blood cell component W1 from the SLO moving image M1 as illustrated in FIG. 7C. The identification unit 141 stores the acquired pieces of eye feature data in the storage unit 130. If needed, the identification unit 141 transmits the eye feature data to the data server 40.

A procedure by which the flow rate specification unit (second identification unit) 1412 acquires information on the blood flow rate will be described. The flow rate specification unit 1412 detects retinal vessel shadow areas SH from the SLO moving image M1 (second SLO image). Specifically, the flow rate specification unit 1412 performs differential processing between adjoining frames of the SLO moving image M1, examines pixel values at each set of x and y positions in the frame direction, and determines a standard deviation of the pixel values. The flow rate specification unit 1412 detects areas where the standard deviation has a value higher than or equal to a threshold T1 as vessel shadow areas SH.

Next, the flow rate specification unit (second identification unit) 1412 detects high luminance blood cell components from the retinal vessel shadow areas SH by using an arbitrary publicly-known image processing technique. In the present exemplary embodiment, the flow rate specification unit 1412 detects areas that have an area size smaller than or equal to a threshold T3 and a circularity degree greater than or equal to a threshold T4, among areas that have luminance higher than or equal to a threshold T2 in the retinal vessel shadow areas SH, as high luminance blood cell components W2.

In the present exemplary embodiment, the flow rate specification unit (second identification unit) 1412 identifies high-luminance points that flow through a vessel as blood cell components, without directly determining a flow rate. However, this is not restrictive and the flow rate specification unit 1412 may identify a blood flow rate.

In step S630, the decision unit 142 decides whether it is necessary to capture an SLO still image M2 with a different focus position, based on the eye features acquired in step S620. In other words, the decision unit 142 decides whether an SLO still image M2 needs to be captured because a vessel shape identified from the SLO moving image M1 is abnormal.

In the present exemplary embodiment, the eye features are the retinal vessel shadow areas SH and the high luminance blood cell component W1 in the SLO moving image M1. The decision unit 142 thins the retinal vessel shadow areas SH into curves, and measures the diameter D1 of the retinal vessel shadows at each position of the curves. If the measurements of the diameter D1 of the retinal vessel shadows include a value less than a threshold Ts or greater than a threshold Ta, the decision unit 142 decides that it is not possible to identify vessel areas from the SLO moving image M1, and decides that it is necessary to capture an SLO still image M2 with a different focus position. This can reduce the possibility that the vessel diameter is underestimated or overestimated which causes misidentification of vessels.

It should be noted that the vessel shape being abnormal means only that the shape of a vessel identified in the SLO moving image M1 is abnormal, but not necessarily that the examinee has abnormal retinal vessels. Examples include a case where the SLO moving image M1 has low image quality because of involuntary eye movements during fixation.

If the decision unit 142 decides that re-imaging is needed (YES in step S630), then in step S640, the determination unit 180 determines parameters related to the re-imaging focus depth. The parameters for changing the focus position may include the following:
(i) the number of new focus positions to be set;
(ii) the range of variation of focus positions;
(iii) the interval(s) of variation of focus positions; and
(iv) focus positions.

In the present exemplary embodiment, the determination unit 180 acquires in advance normal values of the thicknesses of respective layers that constitute the retina 227, from the data server 40. Boundaries of retinal vessels are clearly observable near the nerve fiber layer. The determination unit 180 therefore sets a new focus position F2 near the nerve fiber layer, i.e., to a position approximately 200 µm on the inner-layer side from the focus position F1. As a result, the number of new focus positions to be set is one, the range of variation is 200 µm, the interval of variation is 200 µm, and the focus position is F1−200 µm. If the decision unit 142 decides in step S630 that the focus position need not be changed (NO in step S630), the processing proceeds to step S650 described later.

In step S640, the imaging instruction unit 100 acquires the parameters of the focus depth determined by the determination unit 180 and other imaging conditions from the operation unit 170 or the storage unit 130. The imaging instruction unit 100 transmits the imaging conditions and a resulting imaging instruction signal to the eye image capturing device 20. According to the received imaging instruction signal, the eye image capturing device 20 captures an SLO image of the eye based on the instructed conditions.

The eye image capturing device 20 acquires a new SLO still image M2 based on the parameters related to the changing of the focus position, determined in step S640. In the present exemplary embodiment, as illustrated in FIG. 7B, the eye image capturing device 20 acquires an SLO still image M2 whose focus position F2 is set near the nerve fiber layer by using signal light that has a focus position shallower than the SLO moving image M1. It should be noted that the retinal vessel shadow areas SH on the SLO moving image M1 that is acquired at the focus position F1 near the boundary between inner and outer segments of visual cells correspond to retinal vessel areas BV on the SLO still image M2 that is acquired at the focus position F2 near the nerve fiber layer.

In another example, the user may wish to confirm imaging condition settings before re-imaging. In that case, after the decision unit 142 decides that re-imaging is needed (YES in step S630), the image processing device 10 may issue a notification to confirm whether re-imaging may be performed. In such a case, the image processing device 10 makes the display unit 160 show a button for instructing whether to perform re-imaging, along with the notification. The user operates the operation unit 170, and based on the resulting instruction information, the image processing device 10 determines whether to perform re-imaging.

In another example, after the determination unit 180 sets the parameters of the focus position, the display control unit 144 makes the display unit 160 show imaging conditions including the parameters of the focus position so that the user can make changes. The display control unit 144 also makes the display unit 160 show a button for instructing the imaging. Thus, after the user changes the imaging conditions based on the image captured by the first imaging, the image processing device 10 can instruct the eye image capturing device 20 to perform imaging according to a user instruction.

In step S610 (second round), the SLO image acquisition unit 110 acquires an SLO still image M2. The image processing device 10 then proceeds to step S620 (second round) to acquire eye features from the SLO still image M2.

In step S620 (second round), the identification unit 141 acquires retinal vessel areas BV from the SLO still image M2 (first SLO image) that is acquired in step S610 (second round). In the present exemplary embodiment, the identification unit 141 detects retinal vessel areas BV from the SLO still image M2 by using an arbitrary publicly-known line enhancement filter. After the processing of detecting retinal vessel area BV, the image processing device 10 proceeds to step S650 for arithmetic processing.

In step S650, the acquisition unit 143 performs an arithmetic operation using the SLO moving image M1 acquired at the focus position F1 and the SLO still image M2 acquired at the focus position F2. The acquisition unit 143 thereby measures the behavior (or form) of eye cells (or tissue).

The information to be identified in the present exemplary embodiment is information on a blood flow in vessels. The information to be identified includes at least any of the following: information on an occluded position of a vessel, information on the amount of blood flow in a vessel, and information on the maximum blood flow rate and minimum blood flow in a vessel. The acquisition unit 143 compares vessel areas with areas where blood actually flows through vessels, thereby determining vessel areas without a blood flow and identifying occluded positions of vessels.

The acquisition unit 143 also acquires information on thickness from vessel areas, and combines the information with information on a blood flow rate to measure the amount of blood flow per unit time. The acquisition unit 143 continuously measures the amount of blood flow on the SLO moving image M1 for a certain period, to acquire variations in the amount of blood flow. The acquisition unit 143 thereby acquires information on the maximum blood flow rate and minimum blood flow rate. Specific procedures for measurement will be described in detail later.

In step S660, the display control unit 144 makes the display unit 160 show an eye image or images acquired in step S610 and the measurement result of the behavior (or form) of eye cells (or tissue) calculated by the acquisition unit 143 in step S650. In the present exemplary embodiment, the display control unit 144 makes the display unit 160 show the SLO moving image M1 as an eye image. As the measurement result, the display control unit 144 makes the display unit 160 show a graph of the moving speed of the high luminance blood cell component W1 and indexes of blood flow behavior which are calculated based on the moving speed.

Figure 8A:
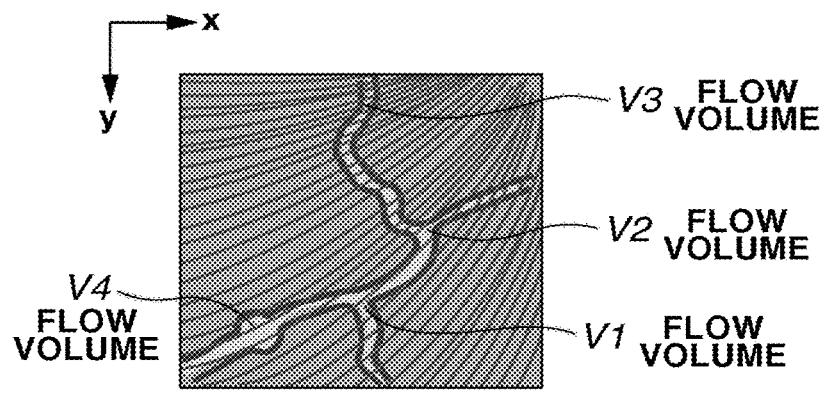
FIGS. 8A, 8B, 8C, and 8D are diagrams illustrating a result of image processing according to an exemplary embodiment.
Figure 8B:
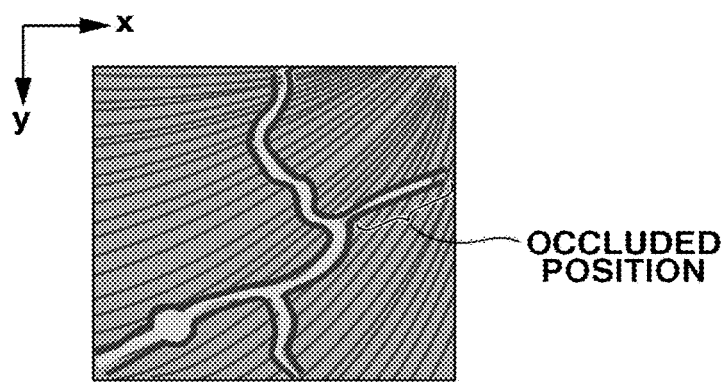
Figure 8C:
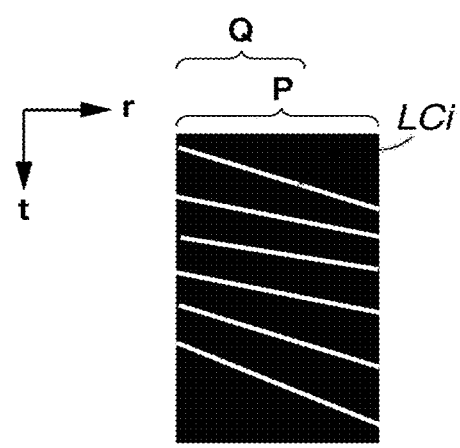
Figure 8D:
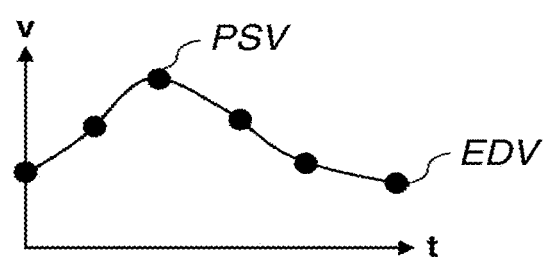

FIGS. 8A to 8D are diagrams illustrating information that the display control unit 144 shows on the display unit 160. FIG. 8A illustrates an image that displays the amounts of blow flow per unit time at certain positions of vessels. FIG. 8B illustrates an image that displays an occluded position of a vessel. FIG. 8C illustrates an example of a spatiotemporal image that is obtained by clipping the SLO moving image M1 along a path P on a vessel. FIG. 8D illustrates an example of a graph of a blood flow velocity. The display contents are not limited thereto. Any images, image processing results, measurement values, and measurement indexes may be displayed.

In step S670, the instruction acquisition unit 150 acquires from outside an instruction on whether to store the measurement result output by the acquisition unit 143 in step S650 in the data server 40. For example, an operator inputs such an instruction through the keyboard 306 and/or the mouse 307. If there is an instruction to store the measurement result (YES in step S670), the processing proceeds to step S680. If not (NO in step S670), the processing proceeds to step S690.

In step S680, the image processing unit 140 transmits the examination date and time, information that identifies the eye to be examined, and the measurement result to the data server 40 in association with each other.

In step S690, the instruction acquisition unit 150 acquires from outside an instruction on whether to end the SLO image measurement processing of the image processing device 10. Such an instruction is input by the operator through the keyboard 306 and/or the mouse 307. If an instruction to end the processing is acquired (YES in step S690), the image processing device 10 ends the SLO image measurement processing. If an instruction to continue the processing is acquired (NO in step S690), the processing returns to step S610. The image processing device 10 then performs processing on a next eye to be examined (or re-processing on the same eye to be examined).

Next, the processing to be performed in step S650 will be described in detail with reference to the flowchart of FIG. 9.

In step S910, the measurement position setting unit 1431 sets measurement positions for measuring a blood flow rate based on the eye features acquired in step S620 (in first and second rounds). In the present exemplary embodiment, the measurement position setting unit 1431 employs measurement positions that are acquired by the instruction acquisition unit 150. Specifically, the measurement position setting unit 1431 employs a path Q of FIG. 7C. It should be noted that measurement positions need not necessarily be manually specified and may be automatically set based on eye features. For example, a retinal vessel shadow area SH that is acquired by the identification unit 141 in step S620 can be thinned into a vessel center line P. The measurement position setting unit 1431 may use the vessel center line P as measurement positions.

In step S920, the image feature selection unit 1433 selects image features to be used for measurement from among the eye features that are acquired by the identification unit 141 in step S620. In the present exemplary embodiment, the image feature selection unit 1433 selects the high luminance blood cell component W1 in the SLO moving image M1 from among the eye features acquired in step S620 (first round). The high-luminance moving body in the image will be assumed to be a white blood cell. The image feature selection unit 1433 calculates the degree of abnormality Ia of detected retinal vessel shadow areas SH at each position Pi on vessel centerlines P. Suppose that the degree of abnormality Ia at a measurement position Pi is lower than a certain value. The image feature selection unit 1433 selects retinal vessel shadow areas SH within a certain distance from such a measurement position Pi as image features for measurement (without referring to image features of the SLO still image M2). On the other hand, if the degree of abnormality Ia at a measurement position Pi is higher than or equal to the certain value, the image feature selection unit 1433 refers to the SLO still image M2. The image feature selection unit 1433 selects retinal vessel shadow areas SH within a certain distance from the measurement position Pi as image features for measurement only if the pixel at the same x and y positions on the SLO still image M2 belongs to a retinal vessel area BV.

Any publicly-known indexes may be used as the degree of abnormality Ia. The present exemplary embodiment uses the square of a residual between an average value Da of normal vessel diameters and the diameter D1 of a retinal vessel shadow area SH, measured at each position Pi on a curve that is obtained by thinning the retinal vessel shadow area SH. If a vessel candidate area (retinal vessel shadow area SH) detected on the SLO moving image M1 with the focus position F1 set near visual cells C has low reliability, the image feature selection unit 1433 refers to image features detected on the SLO still image M2. This enables more accurate measurement of vessel diameters on the SLO moving image M1.

In step S930, the measurement unit 1434 measures the behavior (or form) of eye cells (or tissue) by using the image features selected in step S920. In the present exemplary embodiment, the measurement unit 1434 measures the moving speed of a white blood cell by using the following image features: the high luminance blood cell component W1 on the SLO moving image M1 selected in step S920; and vessel candidate areas (retinal vessel shadow areas) SH on the SLO moving image M1 that are positionally associated with retinal vessel areas BV on the SLO still image M2.

Figure 9A:
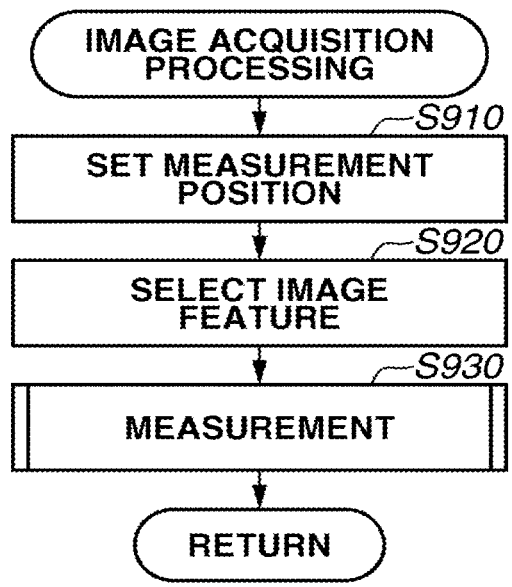
FIGS. 9A and 9B are flowcharts illustrating details of processing performed in step S650.
Figure 9B:
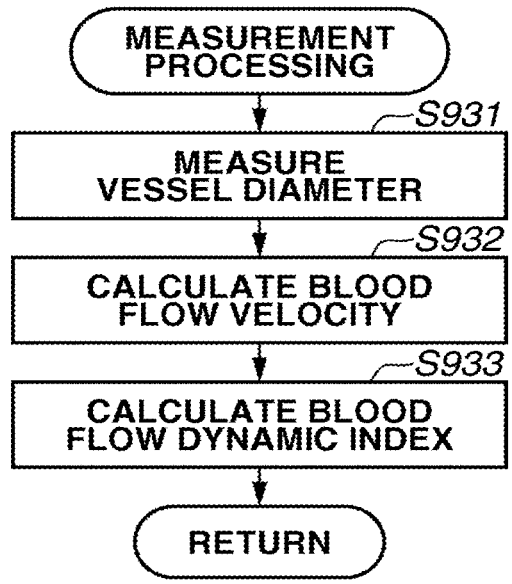

Referring to FIG. 9B, the processing performed in step S930 will be described in detail.

In step S931, the measurement unit 1434 measures the vessel diameter of the retinal vessel shadow areas SH acquired by the identification unit 141. Specifically, as illustrated in FIG. 7C, the measurement unit 1434 examines each position Pi on vessel center lines P that are obtained by thinning the retinal vessel shadow areas SH, for luminance values in a direction perpendicular to the vessel center line P. The measurement unit 1434 determines the distance of the range where luminance values are higher than or equal to a threshold T5, as the vessel diameter D1.

In step S932, the measurement unit 1434 calculates a blood flow velocity v based on the high luminance blood cell component W1 on the SLO moving image M1 selected in step S920. Specifically, the measurement unit 1434 acquires an adjacent interframe velocity vi on the measurement path Q that is set in step S910:

$vi$=the moving distance[mm] of the high luminance blood cell component×frame rate $k$[1/sec].

In step S933, the measurement unit 1434 calculates indexes related to blood cell behavior based on the values of the vessel diameter calculated in step S931 and the blood flow velocity v calculated in step S932. In the present exemplary embodiment, the measurement unit 1434 calculates a pulsatility index (PI), a resistance index (RI), and the amount of blood flow (FL) as blood flow behavior indexes by using the following equations:

pulsatility index PI=(PSV−EDV)/$Va$;

resistance index RI=(PSV−EDV)/PSV; and the amount of blood flow FL[ml/min]=0.06×blood flow velocity[mm/sec]×vessel cross-sectional area[mm$^2$], where
PSV=peak systolic velocity,
EDV=end diastolic velocity, and
Va=average blood flow velocity.
The pulsation period and the positions of the systolic phase and end diastolic phase are determined based on pulse wave data. The pulse waves employed herein refer to a waveform representation of volume changes caused by blood flowing into a certain portion of the body. Pulse waves can be measured by capturing vasomotor responses.

The vessel cross-sectional area is a value calculated based on the value of the vessel diameter (on the assumption that the vessel has a circular cross section). Such indexes enable quantitative evaluation of the flowability of blood in the measurement position and the amount of blood supply per unit time.

With the configuration described above, the image processing device 10 measures a blood flow from an SLO moving image M1 that is captured with a focus set near the boundary between inner and outer segments of visual cells. During the measurement, the image processing device 10 determines whether it is necessary to capture an SLO image with a different focus position, according to the degree of abnormality Ia of vessel candidate areas SH detected.

If it is determined to be necessary to change the focus position for re-capturing, the image processing device 10 changes the focus position to near the nerve fiber layer and makes the eye image capturing device 20 capture an SLO still image M2. If vessel candidate areas SH of the SLO moving image M1 include a location of low reliability, the image processing device 10 examines the same x and y positions of the SLO still image M2. The image processing device 10 then calculates the behavior of white blood cells treating areas that are detected as vessel candidate areas SH on both the SLO images, as retinal vessel areas BV. This enables more accurate measurement of the behavior of white blood cells on the SLO moving image M1 whose focus position F1 is set near visual cells C.

According to the present exemplary embodiment, whether to re-capture an SLO image is decided and re-imaging parameters are determined, based on image information. This can reduce work load on the user of the SLO imaging device. It is also possible to reduce imaging time which is binding time for the subject.

In the first exemplary embodiment, when a focus position is changed to re-capture an SLO image, the image processing device 10 performs an arithmetic operation between image features at respective positions of SLO images captured at different focus positions. The first exemplary embodiment is intended thereby to improve the accuracy of measurement. A second exemplary embodiment is intended to select types of image features suited to (an analysis based on) images acquired at respective focus positions, and combine results of detection of respective selected image features to calculate measurement indexes, thereby measuring the form and/or behavior of eye tissue and/or cells more accurately.

An SLO still image M2 whose focus position is set to the nerve fiber layer enables accurate observation of boundaries of retinal vessels. However, it is sometimes difficult to acquire information inside the vessels, such as a blood flow rate, since vessel walls produce high luminance. An SLO moving image M1 whose focus position is set to visual cells C enables observation of the moving loci of white blood cells with higher contrast. It is difficult, however, to accurately identify vessel areas since vessels are not in focus.

Information both on vessel areas and a blood flow rate need to be acquired in order to measure blood flow behavior.

In the present exemplary embodiment, in order to accurately measure a blood flow velocity in capillary vessels, an image processing device 10 initially acquires a plurality of SLO still images M2 (first SLO images) with a focus position F2 set to the nerve fiber layer, and identifies retinal vessel areas BV (first tissue). The image processing device 10 then applies a filter to the SLO images, attempting to identify a high luminance body (second tissue) that flows through the vessels. Instead of SLO still images, an SLO moving image may be acquired to identify a high luminance body. Even if a high luminance body itself fails to be identified, the image processing device 10 identifies temporal changes in luminance inside the vessels, thereby identifying information on a blood flow rate or the like.

If information on a blood flow rate is determined to be as unidentifiable, the image processing device 10 determines that the focus position needs to be changed in order to acquire the moving loci of blood cell components which are needed for blood flow measurement. The image processing device 10 then acquires an SLO moving image M1 with the focus position set near the boundary between inner and outer segments of visual cells. As an eye feature, the image processing device 10 detects the moving loci of white blood cell components from the SLO moving image M1. The image processing device 10 measures vessel diameters D2 from retinal vessel areas BV, measures a blood flow velocity v from the moving loci of white blood cell components, and calculates blood flow behavior indexes based on the measurements. The image processing device 10 thereby measures the form and/or behavior of eye tissue and/or cells with higher accuracy.

A functional block diagram of the image processing device 10 according to the present exemplary embodiment is basically the same as FIG. 1. A difference from the first exemplary embodiment lies in that the image feature selection unit 1433 is included in the identification unit 141. The image processing unit 140 retains list data called eye feature list FD in advance. The eye feature list FD lists types of eye features suited to analysis (or observation) for respective values of focus positions (or layer types) such as illustrated in FIG. 7D.

FIG. 7D will be described. FIG. 7D illustrates an eye feature list FD that contains the types of layers corresponding to respective focus positions and eye features that can be most clearly observed when a focus position is set to the layers. When a layer shape is normal, the image processing device 10 may select eye features based on the focus position. If a layer shape abnormality is present as in the subsequent exemplary embodiments, the image processing device 10 selects eye features based on the layer type instead of the focus position. The focus position is represented in the Figure by F1. However, it is not limited to F1. For example, it can also be represented by F2. An image processing procedure according to the present exemplary embodiment is as illustrated in FIG. 6. The image processing procedure is the same as the first exemplary embodiment except steps S610, S620, S630, S640, and S650. Description of the same part will be omitted.

In step S610, the SLO image acquisition unit 110 acquires an SLO still image M2 whose focus position F2 is set to the nerve fiber layer. FIG. 7B illustrates an example of the SLO still image M2. Boundaries of retinal vessels can be clearly observed. Since the interior of the retinal vessels has high luminance on the whole, a grain-like area W2 that represents a white blood cell does not have high contrast to the background.

In step S620, the identification unit 141 acquires eye features from the SLO still image M2 acquired at the focus position F2. In the present exemplary embodiment, the image feature selection unit 1433 refers to the eye feature list FD, and automatically selects the type of eye features to acquire according to the value of the focus position F2 of the SLO still image M2. Specifically, the image feature selection unit 1433 selects retinal vessel areas BV as eye features based on the focus position F2 (near the nerve fiber layer) of the SLO still image M2. The area specification unit (first identification unit) 1411 acquires retinal vessel areas BV from the SLO still image M2. It should be noted that the method of acquiring eye features is not limited thereto. For example, the area specification unit 1411 may acquire eye features of a type that is instructed from the instruction acquisition unit 150.

The identification unit 141 stores pieces of eye feature data detected into the storage unit 130. If needed, the identification unit 141 transmits the eye feature data to the data server 40.

In step S630, the decision unit 142 decides whether the focus position needs to be changed. The decision unit 142 decides whether the focus position needs to be changed, according to the focus position F2 of the SLO still image M2 and the type of eye features acquired from the SLO still image M2. The decision unit 142 applies a filter preset to the SLO still image M2, attempting to identify a high luminance body (second tissue) flowing through the vessels. Instead of an SLO still image, an SLO moving image may be acquired to identify a high luminance body. If a high luminance body itself fails to be identified, the decision unit 142 identifies temporal changes in luminance inside the vessels, thereby identifying information on a blood flow rate. If such information fails to be identified, the decision unit 142 refers to the table of FIG. 7D and decides that the focus position F2 needs to be changed to the focus position F1 near the boundary between inner and outer segments of visual cells in order to obtain blood cell features.

In step S640, the determination unit 180 determines parameters related to changing a focus position. The parameters for changing a focus position include the following:
(i) the number of new focus positions to be set;
(ii) the range of variation of focus positions;

(iii) the interval (s) of variation of focus positions; and
(iv) focus positions.

In the present exemplary embodiment, the determination unit 180 determines values as follows: (i) 1, (ii) 200 µm, and (iii) 200 µm. The determination unit 180 also determines that (iv) the new focus position F1 is F2+200 µm. It should be noted that the method of changing a focus position is not limited thereto. For example, the user may instruct from the instruction acquisition unit 150 whether a focus position needs to be changed. The user may specify the parameter values for changing a focus position.

In step S610 (second round), the SLO image acquisition unit 110 acquires a new SLO moving image M1 by using the parameters for changing a focus position, determined by the determination unit 180. Since in step S640 the focus position of the SLO moving image M1 is set near the boundary between inner and outer segments of visual cells, i.e., near F2+200 µm, the resulting SLO moving image M1 is as illustrated in FIG. 7C. The boundaries of retinal vessel shadow areas SH blur, whereas a grain-like high luminance area W1 that represents a white blood cell can be observed and analyzed with high contrast in the image.

In step S620 (second round), the flow rate specification unit (second identification unit) 1412 acquires eye features from the newly acquired SLO moving image M1. In the present exemplary embodiment, the flow rate specification unit 1412 acquires the moving locus of a high luminance blood cell component W1 by the following procedures:

(i) Generate a spatiotemporal image; and
(ii) Detect linear areas on the spatiotemporal image.

(i) The flow rate specification unit 1412 determines a vessel center line P by thinning an area that has the same x and y coordinates as those of an area where retinal vessels are present, i.e., a retinal vessel area BV on the SLO still image M2. As illustrated in FIG. 8C, the flow rate specification unit 1412 then generates a spatiotemporal image with position r along the vessel center line P as the horizontal axis and time t as the vertical axis. The spatiotemporal image is equivalent to a curved cross section with respect to time of the SLO moving image M1 taken along the path P. Time t is determined by dividing the frame number i of the SLO moving image M1 by the frame rate k [1/sec]. The spatiotemporal image includes a plurality of high luminance linear components LCi each indicating the moving distance of a blood cell component.

(ii) The flow rate specification unit 1412 detects the high luminance linear areas LCi on the spatiotemporal image. The flow rate specification unit 1412 uses an arbitrary publicly-known line enhancement filter to enhance lines, and binarizes the resultant with a threshold Tt for detection.

In step S650, the measurement unit 1434 measures the behavior of blood cells by using retinal vessel areas BV and the moving loci of white blood cells. The retinal vessel areas BV are eye features acquired from the SLO still image M2 which is acquired at the focus position F2. The moving loci of white blood cells are acquired from the SLO moving image M1 which is acquired at the focus position F1. Referring to FIG. 9A, the processing performed in step S650 will be described in detail.

In step S910, the measurement position setting unit 1431 sets measurement positions for measuring a blood flow rate based on the eye features acquired in step S620. In the present exemplary embodiment, the measurement position setting unit 1431 employs measurement positions that are acquired from the instruction acquisition unit 150. Specifically, the measurement position setting unit 1431 employs the path Q of FIG. 7C. It should be noted that measurement positions need not necessarily be manually specified, and may be automatically set based on eye features. For example, retinal vessel areas BV that are acquired by the identification unit 141 in step S620 can be thinned into vessel center lines P. The measurement position setting unit 1431 may use the vessel center lines P as measurement positions. In the present exemplary embodiment, the processing skips step S920 and proceeds to step S930 since image features are already selected.

In step S930, the measurement unit 1434 measures the behavior (or form) of eye cells (or tissue) by using the eye features acquired from the SLO moving image M1 and the SLO still image M2. In the present exemplary embodiment, the measurement unit 1434 measures the moving speed of a white blood cell by using the retinal vessel areas BV acquired from the SLO still image M2 and the moving locus of the high luminance blood cell component W1 acquired from the SLO moving image M1. Referring to FIG. 9B, the processing performed in step S930 will be described in detail.

In step S931, the measurement unit 1434 measures vessel diameters in the retinal vessel areas BV acquired by the identification unit 141. Specifically, as illustrated in FIG. 7B, the measurement unit 1434 examines each position Pi on vessel centerlines P that are obtained by thinning the retinal vessel areas BV, for luminance values in a direction perpendicular to the vessel center line P. The measurement unit 1434 determines the distance of the range where luminance values are higher than or equal to a threshold T6 as a vessel diameter D2.

In step S932, the measurement unit 1434 calculates a blood flow velocity v based on linear areas LCi detected on the spatiotemporal image. Specifically, the measurement unit 1434 uses a Hough transform to detect a linear area LCi as a straight line, and calculates a blood flow velocity v by using its angle and distance to the coordinate origin. The line detection technique is not limited thereto, and any publicly-known techniques may be used. The horizontal axis of the spatiotemporal image indicates a position r [mm] along the vessel, and the vertical axis indicates time t [sec] when a blood cell component passes the position r. For example, with r=0, plotting time t on the horizontal axis and the blood flow velocity v on the vertical axis produces a graph of the blood flow velocity v like FIG. 8D.

In step S933, the measurement unit 1434 calculates indexes related to blood cell behavior based on the values of the vessel diameters calculated in step S931 and the values of the blood flow velocity v calculated in step S932. The method of calculating the indexes related to blood flow behavior is the same as in the first exemplary embodiment. Description thereof will thus be omitted. With the foregoing configuration, the image processing device 10 selects retinal vessel areas BV from an SLO still image M2 and the moving loci of blood cells from an SLO moving image M1, and combines the results of acquisition of the image features to calculate measurement indexes. This enables more accurate measurement of blood cell behavior in the eye.

Unlike the second exemplary embodiment, a third exemplary embodiment includes acquiring an eye volume image and examining the configuration of layer boundary positions. If layer shapes are deformed, an image processing device 10 according to the present exemplary embodiment determines that a focus position needs to be changed for image capturing. The image processing device 10 acquires a group of SLO still images M2i at different focus positions, and acquires retinal vessel areas. The image processing device 10 selects partial images at focus positions suited to measurement in respective positions on the fundus, and connects retinal vessel areas on the partial images so that blood flow behavior can be measured more accurately.

An overview of the processing will be given with reference to FIGS. 10A to 10D. FIG. 10A illustrates an eye volume image, which shows focus positions F3, F4, F5, and F6 of SLO images. FIG. 10B illustrates an SLO image that is focused on vessel areas, generated by combining SLO images having focus positions F3, F4, and F5. FIG. 10C illustrates an SLO image at the focus position F6, where visual cells C are in focus. FIG. 10D illustrates focus positions of SLO images and image features of tissue that are obtained from the SLO images when a focus is set to the respective positions.

Specifically, the image processing device 10 acquires a group of SLO still images M2$i$ that are captured at different focus positions, based on the position of the boundary of the nerve fiber layer acquired from an OCT volume image. At each position on the fundus, the image processing device 10 selects a partial image whose focus position is set near the boundaries of inner layers of the retina, and detects retinal vessels BV$i$ on each partial image. The image processing device 10 connects the resultant to acquire retinal vessel areas BV.

Like the second exemplary embodiment, the decision unit 142 decides in certain instances that an SLO moving image suited to detecting the moving loci of blood cells needs to be acquired simultaneously with the acquisition of the group of SLO still images M2$i$. The identification unit 141 acquires an SLO moving image M1 whose focus position F6 is set near the boundary between inner and outer segments of visual cells, and detects the moving loci of blood cells on the SLO moving image M1. The identification unit 141 further calculates blood flow behavior indexes by using the retinal vessel areas BV and the moving loci of blood cells.

Diseases such as macular edema can greatly deform the boundaries of inner layers of the retina. Even in such cases, image features (suited to measurement) in SLO still images of respective focus positions can be combined to calculate blood flow behavior indexes for more accurate measurement of blood flow behavior. A functional block diagram of the image processing device 10 according to the present exemplary embodiment is basically the same as in the second exemplary embodiment. Since a layer shape abnormality is observed (unlike the first and second exemplary embodiments), the eye volume image acquisition unit 120 and the partial image selection unit 1432 are employed.

Figure 6:
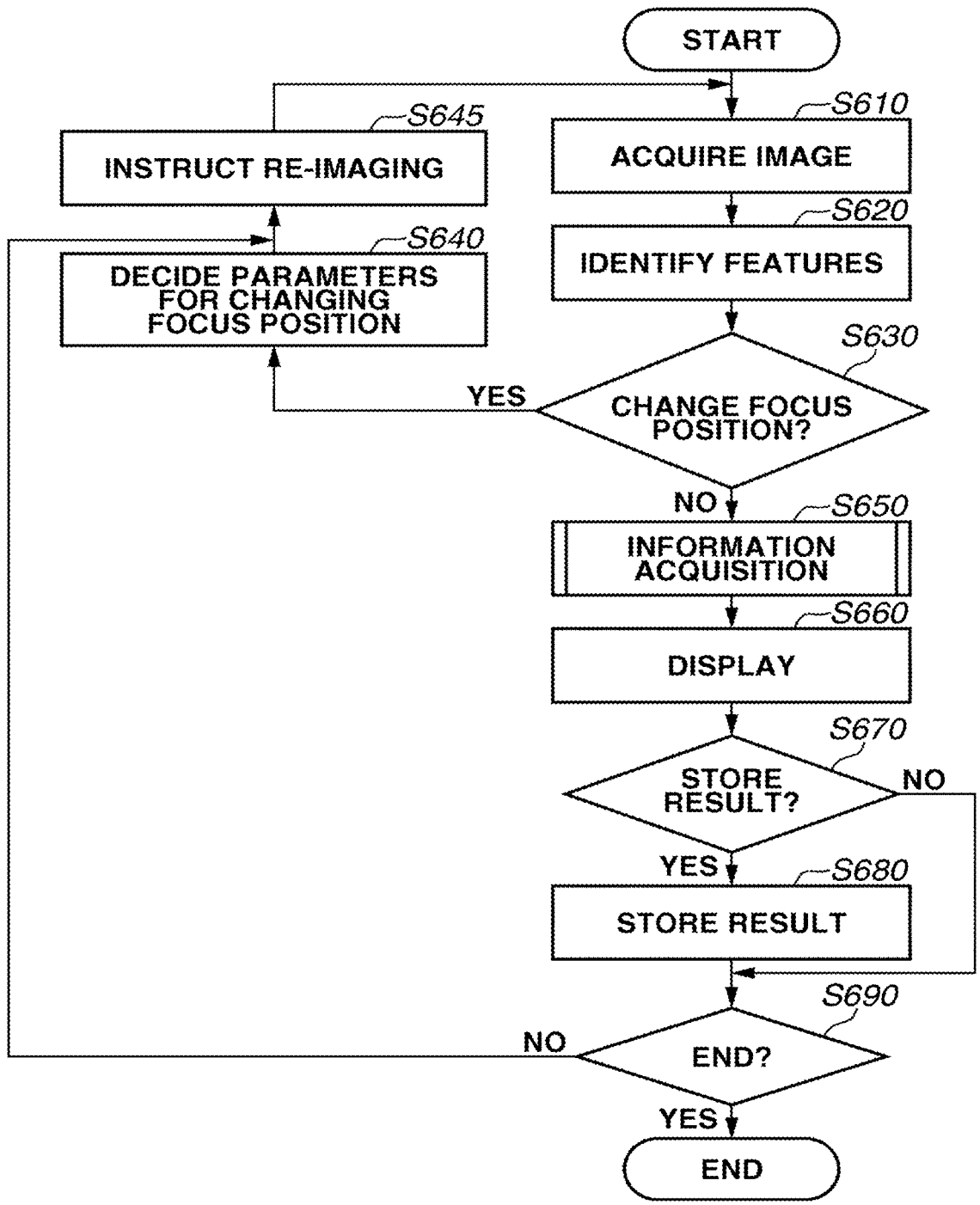
FIG. 6 is a flowchart illustrating processing for an image processing device according to an exemplary embodiment.

An image processing procedure according to the present exemplary embodiment is basically the same as in the second exemplary embodiment (FIG. 6). The image processing procedure is the same as the second exemplary embodiment except steps S610, S620, S630, and S650. In the present exemplary embodiment, description of the processing of steps S640, S660, S670, S680, and S690 will thus be omitted.

In step S610, the eye volume image acquisition unit 120 acquires an eye volume image as illustrated in FIG. 10A from the eye image capturing device 20. The eye volume acquisition unit 120 transmits the eye volume image to the identification unit 141. Suppose that the eye volume image acquired in the present exemplary embodiment includes macular portions as illustrated in FIG. 10A, and the boundaries of inner layers of the retina such as a nerve fiber layer boundary B2 and a boundary B5 between inner and outer segments of visual cells are deformed by macular edema, occurred between the boundary B5 and an outer boundary B6.

In step S620, the identification unit 141 acquires eye features from the eye volume image acquired by the eye volume image acquisition unit 120. As eye features, the identification unit 141 extracts the inner limiting membrane B1, the nerve fiber layer boundary B2, the boundary B5 between inner and outer segments of visual cells, the outer boundary B6 of the retinal pigment epithelium, and retinal vessels (not illustrated). Specifically, the eye volume image to be processed may be regarded as a set of two-dimensional tomographic images (B-scan images). The identification unit 141 then performs the following processing on each of the two-dimensional tomographic images.

The identification unit 141 initially performs smoothing processing on a two-dimensional tomographic image in question, thereby removing noise components. The identification unit 141 then detects edge components from the two-dimensional tomographic image, and extracts several line segments as layer boundary candidates based on their connectivity. The identification unit 141 selects a topmost line segment of the candidates as the inner limiting membrane B1, and a second highest as the nerve fiber layer boundary B2. The identification unit 141 selects a line segment that has the highest contrast among ones lying on the outer-layer side of the inner limiting membrane B1 (in FIG. 10A, on the side of greater Z coordinates) as the boundary B5 between inner and outer segments of visual cells. The identification unit 141 selects a lowest line segment of the layer boundary candidates as the outer boundary B6 of the retinal pigment epithelium.

Using such line segments as initial values, the identification unit 141 may apply Snakes, level-set, or other deformable models for precise extraction. A graph-cut method may be used to detect layer boundaries. Boundary detection using a deformable model or graph cutting may be three-dimensionally performed on the eye volume image, or may be two-dimensionally applied to each of the two-dimensional tomographic images. Any method for detecting layer boundaries may be used as long as the method can detect layer boundaries from tomographic images of the eye.

In step S630, the decision unit 142 decides whether the focus position needs to be changed. In the present exemplary embodiment, the decision unit 142 samples eye features acquired in step S620, on the nerve fiber layer boundary B2, to acquire a row of points. If the row of points includes three adjoining points that form an angle smaller than a certain value, the decision unit 142 decides that there is a layer shape abnormality, i.e., the focus position needs to be changed to acquire an SLO still image.

In step S640, the determination unit 180 determines parameters related to changing a focus position. The determination unit 180 refers to an eye feature list FD, and determines that it is needed to acquire an SLO moving image M1 at the focus position F6 near the boundary between inner and outer segments of visual cells. The purpose of the acquisition of the SLO moving image M1 is to measure blood cell movement which is needed for the measurement of blood flow behavior.

The parameters for changing a focus position include the following:
(i) the number of new focus positions to be set;
(ii) the range of variation of focus positions;
(iii) the interval(s) of variation of focus positions; and
(iv) focus positions.

In the present exemplary embodiment, the determination unit 180 sets focus positions illustrated in FIG. 10A (F3, F4, F5, and F6). More specifically, the determination unit 180 determines the values as follows: (i) 4; (ii) the boundary F6 between inner and outer segments of visual cells–the innermost position F3 of the nerve fiber layer boundary within the capturing range of SLO images; (iii) (the outermost position F5 of the nerve fiber layer boundary within the image capturing range−F3)/2 and F6−F5; and (iv) F3, F4=F3+(F5−F3)/2, F5, and F6.

In the present exemplary embodiment, the determination unit 180 uses information on a fixation target position, acquired in advance from the data server 40, to determine the capturing range of SLO images in the tomographic image.

In step S610, the SLO image acquisition unit 110 acquires SLO still images M2i at the focus positions F3, F4, and F5 which are instructed by the decision unit 142 in step S630. The SLO image acquisition unit 110 also acquires an SLO moving image M1 whose focus position is set near the boundary between inner and outer segments of visual cells.

In step S620, the identification unit 141 detects retinal vessels as eye features from the SLO still images M2i acquired in step S610. The identification unit 141 detects vessels by using an arbitrary publicly-known line enhancement filter. In SLO images, only partial areas are in focus. As long as retinal vessels can be favorably detected from in-focus areas, it is all right that the vessel detection fails in other areas. The flow rate specification unit (second identification unit) 1412 acquires the moving loci of blood cell components as eye features from the SLO moving image M1 acquired in step S610. The method of acquiring the moving loci of blood cell components is the same as in step S620 (first round) of the first exemplary embodiment. Description thereof will thus be omitted in the present exemplary embodiment.

In step S650, the acquisition unit 143 measures the behavior of blood cell components based on the eye features acquired from the SLO still images M2i and the eye features acquired from the SLO moving image M1 which is acquired at the focus position F6 near the boundary between inner and outer segments of visual cells.

Figure 11:
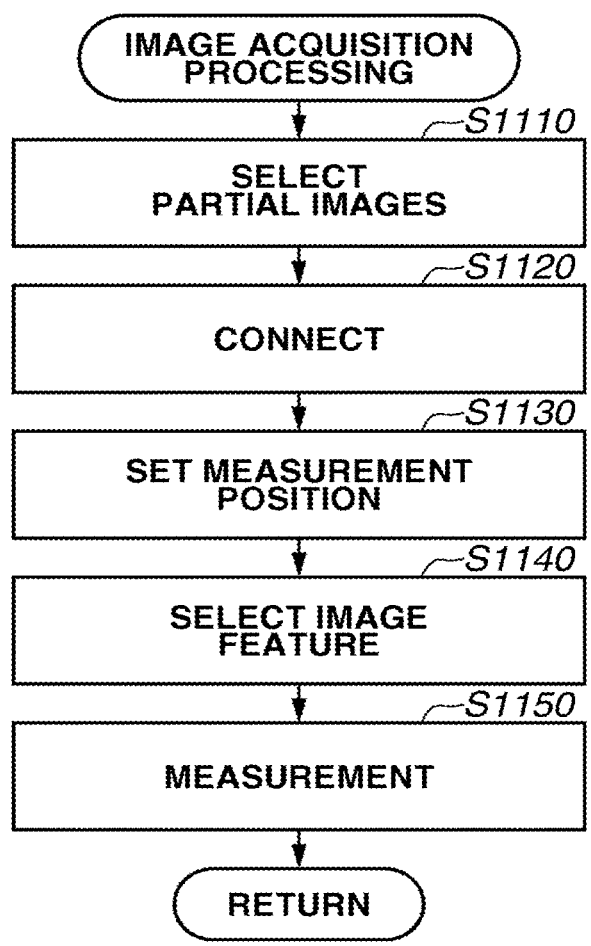
FIG. 11 is a flowchart illustrating details of processing performed in step S650 of the third exemplary embodiment.

Next, the processing performed in step S650 will be described in detail with reference to the flowchart of FIG. 11.

In step S1110, the partial image selection unit 1432 selects partial images based on a distance of focus position from eye features acquired in step S620 (first round), i.e., the nerve fiber layer boundary. At each set of x and y positions within the image capturing range, the partial image selection unit 1432 selects an SLO still image M2i having a nearest matched focus position as a partial image. In the present exemplary embodiment, the partial image selection unit 1432 selects SLO still images M2i that are at smallest distances from the nerve fiber layer boundary in respective sets of x and y positions within the image capturing range. Consequently, the partial image selection unit 1432 selects an area S1 of FIG. 10B from the image of the focus position F3, an area S2 of FIG. 10B from the image of the focus position F4, and an area S3 of FIG. 10B from the image of the focus position F5.

In step S1120, as illustrated in FIG. 10B, the partial image selection unit 1432 connects the partial images (S1, S2, and S3) acquired in step S1110 and the eye features (retinal vessel areas on each partial image) acquired in step S620. In the resulting image, retinal vessels within the image capturing range (S1+S2+S3) are in focus even when a layer shape abnormality is present. Steps S1130, S1140, and S1150 are the same as steps S910, S920, and S930 of the second exemplary embodiment. Description thereof will thus be omitted.

With the foregoing configuration, unlike the second exemplary embodiment, the image processing device 10 acquires an eye volume image and examines the configuration of layer boundary positions. If layer shapes are deformed, the image processing device 10 determines that a focus position needs to be changed for image capturing. The image processing device 10 acquires a group of SLO still images M2i at different focus positions, and acquires retinal vessel areas. The image processing device 10 selects partial images with focus positions suited to measurement in respective positions on the fundus, and connects retinal vessel areas on the partial images for more accurate measurement of blood flow behavior. Diseases such as diabetic macular edema can greatly deform the boundaries of inner layers of the retina. Even in such cases, it is possible to accurately measure blood flow behavior within the image capturing range.

A fourth exemplary embodiment measures visual cells and nerve fibers, not vessels. Visual cells are a part that receives light and obtains a signal in the eye. Nerve fibers are apart that transmits a signal to the brain. An abnormality in either one of the parts is likely to accompany deterioration or a partial or entire loss of the visual function. In the present exemplary embodiment, an image processing device 10 identifies images of visual cells and nerve fibers from SLO images, and displays the image of visual cells and the image of nerve fibers, next to each other or in a switching manner for precise examination of the visual function.

Like the foregoing exemplary embodiments, the hardware configuration according to the present exemplary embodiment is the same as illustrated in FIG. 1. Description thereof will thus be omitted. Description of the processing to be performed by such configuration will also be omitted in a part where the same applies as in the foregoing exemplary embodiments.

Figure 12A:
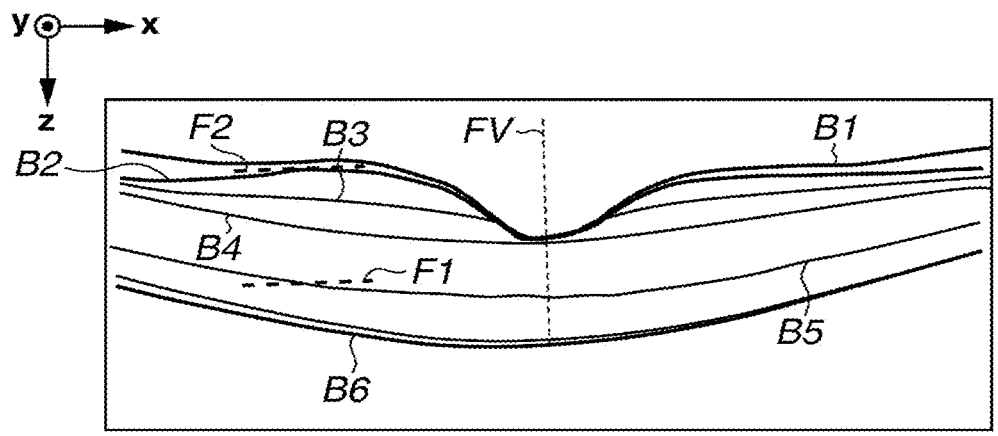
FIGS. 12A, 12B, and 12C are diagrams illustrating an overview of processing according to a fourth exemplary embodiment.
Figure 12B:
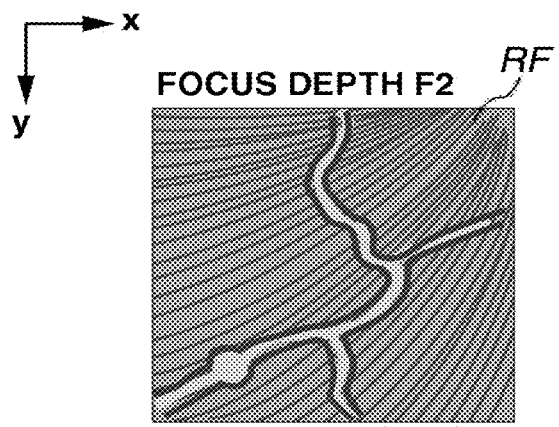
Figure 12C:
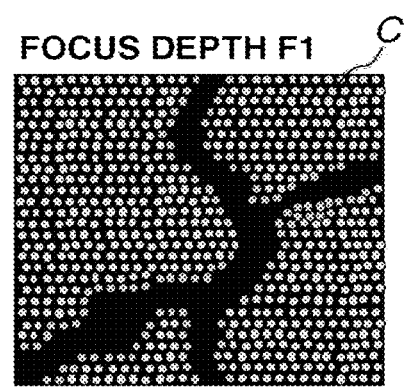

An overview of the processing of the present exemplary embodiment will be given with reference to FIGS. 12A to 12C. FIG. 12A illustrates an OCT tomographic image of a macular portion, showing focus positions F1 and F2 of SLO images. FIG. 12B illustrates an SLO image at a focus depth of F2. FIG. 12C is an SLO image at a focus depth of F1. The focus depth F2 is a value that is determined in order to image a nerve fiber layer RF. The focus depth F1 is a value that is determined in order to image visual cells C. Like the foregoing exemplary embodiments, the values may be determined based on SLO images captured in advance and focus positions thereof. The user may set also the values by manually adjusting focus adjustment mechanisms.

The SLO image acquisition unit 110 acquires such SLO images. The identification unit 141 identifies tissues from the SLO images. The first identification unit 1411 of the identification unit 141 identifies vessel areas from an SLO image of shallow focus position by the processing described in the foregoing exemplary embodiments. The first identification unit 1411 assumes the vessel areas to be outside the nerve fiber layer. The first identification unit 1411 thereby identifies areas where nerve fibers are present. The second identification unit 1412 removes blood-flowing areas from an SLO image of deep focus position to identify visual cell areas. The processing of identifying vessel areas is the same as in the foregoing exemplary embodiments. Description thereof will thus be omitted.

The acquisition unit 143 acquires an SLO image in which nerve fiber areas are identified and an SLO image in which visual cell areas are identified. The display control unit 144 makes the display unit 160 show the images next to each other or in a switching manner. The display control unit 144 identifies abnormal parts of the nerve fibers and abnormal parts of the visual cells, and makes the display unit 160 show the abnormal positions in association with each other.

In another example, the image feature selection unit 1433 of the acquisition unit 143 aligns positions of two SLO images, for example, by utilizing vessel areas seen on the two SLO images. If the instruction acquisition unit 150 acquires an instruction to select an area of one of the images according to an input from the operation unit 170, the acquisition unit 143 identifies the area of the other image that corresponds to the area selected in the one image. The display control unit 144 makes the display unit 160 show the area selected in the one image and the area of the other image corresponding to the selected area, next to each other or in a switching manner.

Figure 13:
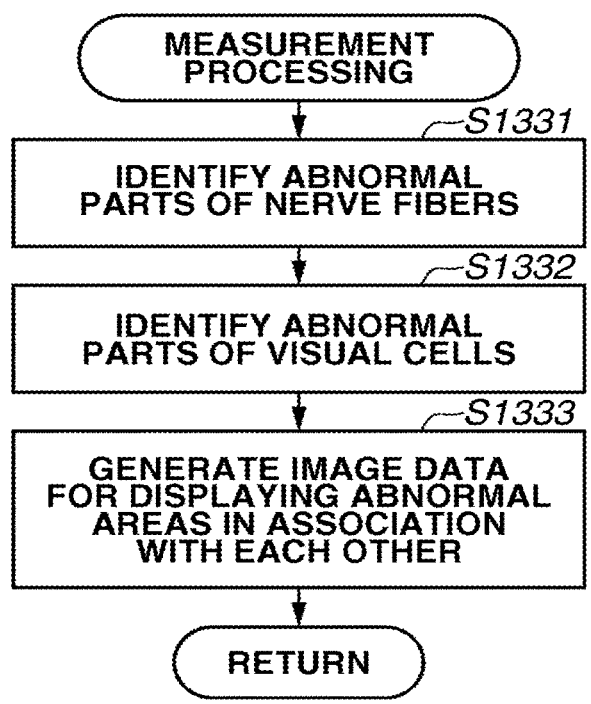
FIG. 13 is a flowchart illustrating details of processing performed in step S930 of the fourth exemplary embodiment.

A processing procedure of the present exemplary embodiment will be described based on the flowchart of FIG. 13. A difference from the first exemplary embodiment lies in that the measurement processing of step S930 (FIG. 9A) included in the information acquisition processing of step S650 (FIG. 6) is changed from the processing illustrated in FIG. 9B to the processing illustrated in FIG. 13.

In step S1331, the measurement unit 1434 identifies abnormal parts of nerve fibers from an image of the focus position F2. The measurement unit 1434 identifies abnormal parts of nerve fibers, for example, by identifying areas where nerve fibers are broken or areas where fibers are locally thinner from the image. In step S1332, the measurement unit 1434 identifies abnormal parts of visual cells from an image of the focus position F1. An example of abnormal parts of visual cells is where visual density of cells is abnormally distributed or the cells are abnormally arranged. The measurement unit 1434 identifies such parts by image analysis.

In step S1333, the display control unit 144 generates image data for displaying the identified abnormal parts in association with each other. For example, the image data is generated such that an SLO image of the focus position F1 and an SLO image of the focus position F2 are displayed next to each other, with additional indications such as boxes which enclose the areas that are identified to be abnormal parts.

In another example, the display control unit 144 makes the display unit 160 show two images in a switching manner according to an input from the operation unit 170 or automatically. In another example, the display control unit 144 generates image data for displaying areas where abnormal parts of two SLO images overlap each other, areas where only nerve fibers are abnormal, and areas where only visual cells are abnormal, in different colors.

The display control unit 144 makes the display unit 160 show the image data generated in step S1333 so that correspondence between abnormal parts of tissues can be displayed in an easily understandable manner.

In the foregoing first to third exemplary embodiments, whether to capture a second SLO image at a different focus position is decided after a first SLO image is captured. However, this is not restrictive. It may be decided in advance to capture SLO images at a plurality of different focus depths. This eliminates the need for the image-dependent decision, and can thus accelerate the processing when information both on vessel areas and a blood flow is not available from a single SLO image.

Exemplary embodiments may be implemented by an image processing device 10 that includes an image processing unit 140, and an imaging control device or imaging instruction device that includes a determination unit 180 which determines imaging conditions based on information from the image processing device 10. The imaging control device or imaging instruction device may include an image processing unit 140.

The foregoing image processing devices 10 are implemented by the cooperation of a computer that includes a CPU and software. However, the functional blocks of an image processing device 10 may be implemented as circuits respectively. Circuit blocks need not necessarily be provided in units of functional blocks. Only some of the functions may be implemented as circuits. A storage medium that contains the software program to be executed by the CPU 301 of an image processing device 10 as described above also constitutes an exemplary embodiment.

An image processing device 10 may be configured as an image processing system that includes a plurality of devices.

The image processing devices 10 acquire features from an OCT tomographic image. However, this is not restrictive. Other images and/or diagnostic devices may be used for structural identification. For example, an image processing device 10 may analyze each of a plurality of SLO images to identify tissue structures to be observed, and select and connect partial images or select any one of the SLO images. Other modalities (imaging devices or measurement devices) may be used to identify tissue structures.

Other Embodiments

Aspects of the present invention can also be realized by a computer of a system or apparatus (or devices such as a CPU or MPU) that reads out and executes a program recorded on a memory device to perform the functions of the above-described embodiment (s), and by a method, the steps of which are performed by a computer of a system or apparatus by, for example, reading out and executing a program recorded on a memory device to perform the functions of the above described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. Each feature disclosed in the description, and (where appropriate) the claims and drawings may be provided independently or in any appropriate combination.

This application claims priority from Japanese Patent Application No. 2011-040272 filed Feb. 25, 2011, which is hereby incorporated by reference herein in its entirety.

What is claimed is:

1. An image processing device comprising:
    a first identification unit configured to identify the spatial configuration of a vessel in an object to be imaged from a first SLO image obtained by signal light that has a first focus position; and
    a second identification unit configured to identify information on a blood flow in at least a part of the identified vessel based on a second SLO moving image obtained by the signal light that has a second focus position deeper than the first focus position,
    wherein the identified vessel in the first SLO image is in focus and the identified vessel in the second SLO moving image is not in focus.

2. The image processing device according to claim 1, wherein the spatial configuration of the vessel comprises the location of the vessel and/or the width of the vessel.

3. The image processing device according to claim 1, wherein the second identification unit identifies at least one of information on an occluded position of the vessel, information on an amount of blood flow of the vessel, or information on a maximum blood flow rate and a minimum blood flow rate of the vessel.

4. The image processing device according to claim 1, further comprising:
    a determination unit configured to determine whether the blood flow rate is identifiable by analyzing the first SLO image; and an instruction unit configured to give an instruction to capture the second SLO moving image if the blood flow rate is determined to be not identifiable.

5. The image processing device according to claim 1, further comprising:
a determination unit configured to decide whether the spatial configuration of the vessel is identifiable by analyzing the second SLO moving image; and
an instruction unit configured to give an instruction to capture the first SLO image if the spatial configuration is determined to be not identifiable.

6. The image processing device according to claim 1, further comprising a display control unit configured to display information on the blood flow of the vessel.

7. An image processing device comprising:
a first image acquisition unit configured to acquire an SLO image of an object to be imaged at a first focus position by using an SLO imaging device;
a determination unit configured to determine whether a predetermined tissue feature existing in the object to be imaged is identifiable by analyzing the SLO image of the object to be imaged acquired at the first focus position;
a decision unit configured to decide a second focus position of the SLO imaging device based on the predetermined tissue feature and the first focus position of the SLO image in a case where the predetermined tissue is determined to be not identifiable;
a second image acquisition unit configured to acquire a second SLO image of the object at the second focus position by using the SLO imaging device; and
an identification unit configured to identify the predetermined tissue feature in the first SLO image or the second SLO image,
wherein the second focus position is different from the first focus position in a depth direction.

8. The image processing device according to claim 7, wherein the predetermined tissue feature is either an area or a blood flow rate of a vessel.

9. The image processing device according to claim 7, further comprising an identification unit configured to identify a first tissue feature existing in the object to be imaged based on the SLO image acquired by the first image acquisition unit,
wherein the predetermined tissue feature comprises a second tissue feature different from said first tissue feature, and wherein the determination unit determines whether said second tissue feature existing in the object to be imaged is identifiable based on the first SLO image.

10. The image processing device according to claim 9, wherein the first tissue feature is a feature for identifying a blood flow rate, and the second tissue feature is a feature for identifying a vessel.

11. An imaging system comprising:
the image processing device according to claim 1; and
an imaging unit configured to capture the SLO image(s).

12. An image processing method comprising:
identifying the spatial configuration of a vessel in an object to be imaged from a first SLO image obtained by signal light that has a first focus position; and
identifying information on a blood flow in at least a part of the identified vessel based on a second SLO moving image obtained by the signal light that has a second focus position greater than the first focus position,
wherein the identified vessel in the first SLO image is in focus and the identified vessel in the second SLO moving image is not in focus.

13. An image processing method comprising:
acquiring a first SLO image of an object to be imaged at a first focus position by using an SLO imaging device;
determining whether a predetermined tissue feature existing in the object to be imaged is identifiable by analyzing the first SLO image of the object to be imaged acquired at the first focus position;
deciding a second focus position of the SLO imaging device based on the predetermined tissue feature and the first focus position of the SLO image in a case where the predetermined tissue is determined to be not identifiable;
acquiring a second SLO image of the object at a second focus position by using the SLO imaging device, and
identifying the predetermined tissue feature in the first SLO image or the second SLO image,
wherein the second focus position is different from the first focus position in a depth direction.

14. An image processing method comprising:
acquiring a first AO-SLO image or sequence of images of an eye to be imaged at a first focus position for imaging nerve fibers in retinal layers;
identifying a first area of the abnormality of the nerve fibers in the first AO-SLO image or the first sequence of images;
acquiring a second AO-SLO image or sequence of images of the eye at a second focus position for imaging visual cells in retinal layers;
identifying a second area of the abnormality of the visual cells in the second AO-SLO image or the second sequence of images; and
generating image data for displaying the first area and second area in association with each other,
wherein the second focus position is different from the first focus position in a depth direction.

15. A program comprising instructions which, when executed by a computer, cause the computer to perform the method of claim 12.

16. A program comprising instructions which, when executed by a computer, cause the computer to perform the method of claim 13.

17. The image processing method according to claim 14, wherein the first area is the area excluding a vessel area from the first AO-SLO image or the first sequence of images, and the second area is the area excluding a blood-flowing area from the second AO-SLO image or the second sequence of images.

* * * * *